(12) United States Patent
Toji

(10) Patent No.: US 9,888,906 B2
(45) Date of Patent: Feb. 13, 2018

(54) ULTRASOUND DIAGNOSTIC APPARATUS, ULTRASOUND IMAGE PROCESSING METHOD, AND NON-TRANSITORY COMPUTER READABLE RECORDING MEDIUM

(71) Applicant: KONICA MINOLTA, INC., Chiyoda-ku, Tokyo (JP)

(72) Inventor: Bumpei Toji, Hashima (JP)

(73) Assignee: KONICA MINOLTA, INC., Tokyo (JP)

( * ) Notice: Subject to any disclaimer, the term of this patent is extended or adjusted under 35 U.S.C. 154(b) by 569 days.

(21) Appl. No.: 14/567,888

(22) Filed: Dec. 11, 2014

(65) Prior Publication Data

US 2015/0164479 A1 Jun. 18, 2015

(30) Foreign Application Priority Data

Dec. 12, 2013 (JP) .................................. 2013-257207
Dec. 2, 2014 (JP) .................................. 2014-244186

(51) Int. Cl.
*A61B 8/00* (2006.01)
*A61B 8/08* (2006.01)

(52) U.S. Cl.
CPC .............. *A61B 8/5207* (2013.01); *A61B 8/08* (2013.01); *A61B 8/4245* (2013.01); *A61B 8/463* (2013.01); *A61B 8/5215* (2013.01); *A61B 8/5246* (2013.01)

(58) Field of Classification Search
CPC ................ A61B 8/00; A61B 8/02; A61B 8/06
See application file for complete search history.

(56) References Cited

FOREIGN PATENT DOCUMENTS

JP 4677199 B2 4/2011

*Primary Examiner* — Joseph M Santos Rodriguez
(74) *Attorney, Agent, or Firm* — Holtz, Holtz & Volek PC

(57) ABSTRACT

An ultrasound diagnostic apparatus having image processing circuitry including: an ultrasound image generator generating first ultrasound images from reflected ultrasound; a video image acquirer acquiring, from an imaging device, first video images capturing manipulation of a probe performed during generation of the first ultrasound images; a relational recorder recording, onto a recording medium, the first ultrasound images and the first video images, in association with each other; a data reader reading second ultrasound images and second video images from the recording medium, the second ultrasound images generated and recorded onto the recording medium in the past, and the second video images capturing manipulation of the probe performed during generation of the second ultrasound images; and a screen composer composing a screen by arranging the first ultrasound images, the second ultrasound images and the second video images, and displaying the screen on a display device.

6 Claims, 14 Drawing Sheets

FIG. 4

| Subject ID | Examination data | Information of a link to video images | Information of a link to ultrasound images | |
|---|---|---|---|---|
| 1234 | 20110506 | XYZ0010101 | ABC0010101 | Storage data list |
| 1235 | 20110506 | XYZ0010102 | ABC0010102 | |
| 1236 | 20110507 | XYZ0010103 | ABC0010103 | |
| 1237 | 20110510 | XYZ0010104 | ABC0010104 | |
| 1238 | 20110512 | XYZ0010105 | ABC0010105 | Additional information set |

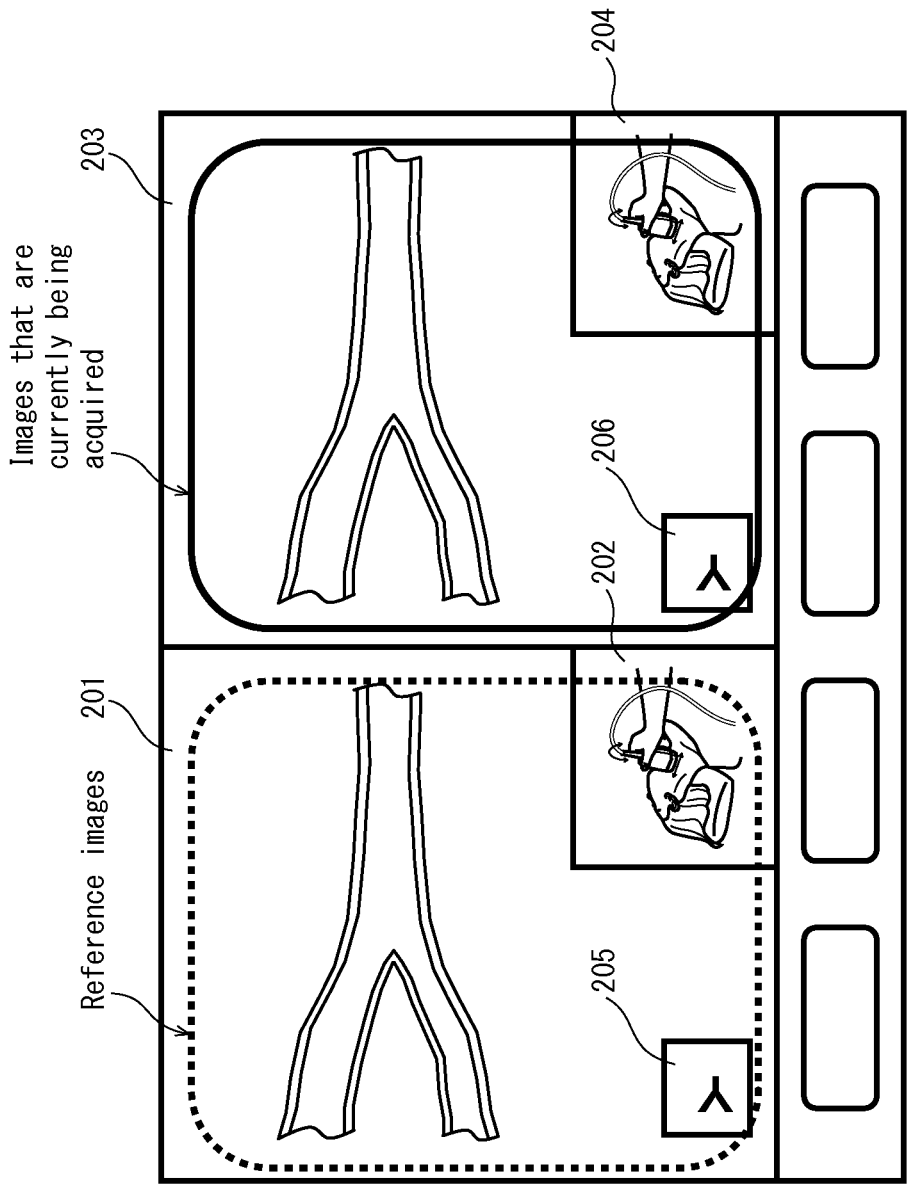

ULTRASOUND DIAGNOSTIC APPARATUS, ULTRASOUND IMAGE PROCESSING METHOD, AND NON-TRANSITORY COMPUTER READABLE RECORDING MEDIUM

CROSS-REFERENCE TO RELATED APPLICATION

This application is based on applications No. 2013-257207 and No. 2014-244186 filed in Japan, the contents of which are hereby incorporated by reference.

BACKGROUND OF THE INVENTION (1) Field of the Invention

The present disclosure relates to ultrasound diagnostic apparatuses and ultrasound image processing methods. In particular, the present disclosure relates to an ultrasound diagnostic apparatus that allows for examination with reference to images acquired by an ultrasound probe based on reflected ultrasound from a subject, and images captured by an imaging device and showing how the examination was performed in the past. The present disclosure also relates to an ultrasound image processing method for the same.

(2) Description of the Related Art

An ultrasound diagnostic apparatus transmits ultrasound to the inside of the subject via an ultrasound probe (hereinafter, "probe"), and receives reflected ultrasound generated due to a difference of acoustic impedance between tissues of the subject. Furthermore, using the reception signal, the ultrasound diagnostic apparatus generates ultrasound cross-sectional images (hereinafter, "ultrasound images") showing the structure of the inner tissues of the subject, and displays the images on a monitor display (hereinafter, "display device"). Ultrasound diagnostic apparatuses are less-invasive, and are capable of displaying the state of the inner tissues in real time in the form of ultrasound images. Therefore, ultrasound diagnostic apparatuses are commonly used for shape diagnostics of living organisms.

In ultrasound examination, ultrasound images of tissues of an examination target part of the subject are compared with ultrasound images of given healthy tissues, thereby examining whether the subject's tissues are healthy or not. By examining the ultrasound images in real time, the examiner can easily identify the body part of the subject to which the probe is applied, and can detect abnormalities in the tissues, if any.

However, when the examiner examines ultrasound images on another occasion after the acquisition of the ultrasound images, the examiner does not have direct information for identifying the body part of the subject to which the probe was applied at the time of the acquisition. This is because no detailed information such as the location of the body part and the angle of the probe applied to the body part is recorded in the ultrasound images when the ultrasound images are acquired. Due to lack of such information, the examiner would not be able to recall the normal state of the tissues to be compared with the subject's tissues. For this reason, in some cases, there have been difficulties in detecting abnormalities in the subject's tissues at a high level of accuracy. In other words, there have been difficulties in ensuring an accurate diagnosis.

In response to this problem, another ultrasound diagnostic apparatus has been proposed and used, which has the function of recording information of the observed body part and the position of the probe during the ultrasound examination, in the form of a body mark and a probe mark respectively, and displaying the marks on the screen together with the ultrasound images. This apparatus enables a person who views the ultrasound images after the ultrasound examination to accurately identify the target body part.

However, this apparatus does not automatically provide body marks or probe marks, and requires that the examiner manually inputs the marks, which necessitates a great amount of labor. For example, in the case of an examination for rheumatoid arthritis, it is proposed to evaluate forty-four finger joints in total. Thus, it is common that a large number of, and a wide variety of body parts need to be examined for a single subject, and such an examination requires a great amount of labor.

In response to this problem, Japanese Patent Publication No. 4677199 proposes an ultrasound diagnostic apparatus which has a camera that captures an image showing the positional relationship between the probe and the subject. This ultrasound diagnostic apparatus generates a composite diagnostic image from the ultrasound image and the captured image, and displays the composite diagnostic images on the screen. This apparatus enables the viewer of the ultrasound images to identify the observed body part after completion of the ultrasound examination, without manually inputting the body marks, etc.

SUMMARY OF THE INVENTION

Problems to be Solved by the Invention

According to the technology proposed in the afore-mentioned patent literature, however, the ultrasound image and the image captured by the camera are combined and recorded as a single still image. Therefore, the viewer cannot know the manipulation of the probe or the movement of the subject performed during the examination in the past.

Since ultrasound images are produced in real time during an ultrasound examination, the examiner often examines the dynamic state of the tissues inside the body while moving the subject's body. In an orthopedic examination for example, the examiner performs an ultrasound examination while repeatedly bending and stretching a joint of the patient. In such cases, in order to perform an ultrasound examination at a high level of accuracy and reproducibility, it is necessary to correctly know the movement of the joint and the manipulation of the probe that were performed during the acquisition of the ultrasound images that are to be used in the comparison observation.

The present disclosure is made in view of the above problems, and aims to provide an ultrasound diagnostic apparatus and an image recording method that enable the examiner to correctly know the movement of the examination target part of the subject and the manipulation of the probe that were performed during the acquisition of the ultrasound images that are to be used in the comparison observation.

Means for Solving the Problems

To solve the problems, one aspect of the present disclosure provides an ultrasound diagnostic apparatus that is connectable to a probe, an imaging device, a recording medium, and a display device, and that obtains and displays ultrasound images of inside a subject's body by transmitting ultrasound towards the subject's body via the probe and receiving reflected ultrasound, the ultrasound diagnostic apparatus comprising image processing circuitry that includes: an ultrasound image generator that generates a sequence of first ultrasound images from the reflected ultrasound; a video image acquirer that acquires, from the imaging device, a sequence of first video images that captures manipulation of the probe performed during generation of the sequence of first ultrasound images; a relational recorder that records, onto the recording medium, the sequence of first ultrasound images supplied from the ultrasound image generator and the sequence of first video images supplied from the video image acquirer, in association with each other; a data reader that reads a sequence of second ultrasound images and a sequence of second video images from the recording medium, the sequence of second ultrasound images being images generated by the ultrasound image generator and recorded onto the recording medium in the past, and the sequence of second video images being video images that capture manipulation of the probe performed during generation of the sequence of second ultrasound images; and a screen composer that composes a screen by arranging the sequence of first ultrasound images, the sequence of second ultrasound images, and the sequence of second video images, and displays the screen on the display device.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIG. 4 is a schematic diagram illustrating an example of a storage data list which is output by a relational recorder 107;

FIG. 14 is a schematic diagram illustrating an example screen displayed by the ultrasound diagnostic apparatus 152.

DESCRIPTION OF THE PREFERRED EMBODIMENT

Figure 1:
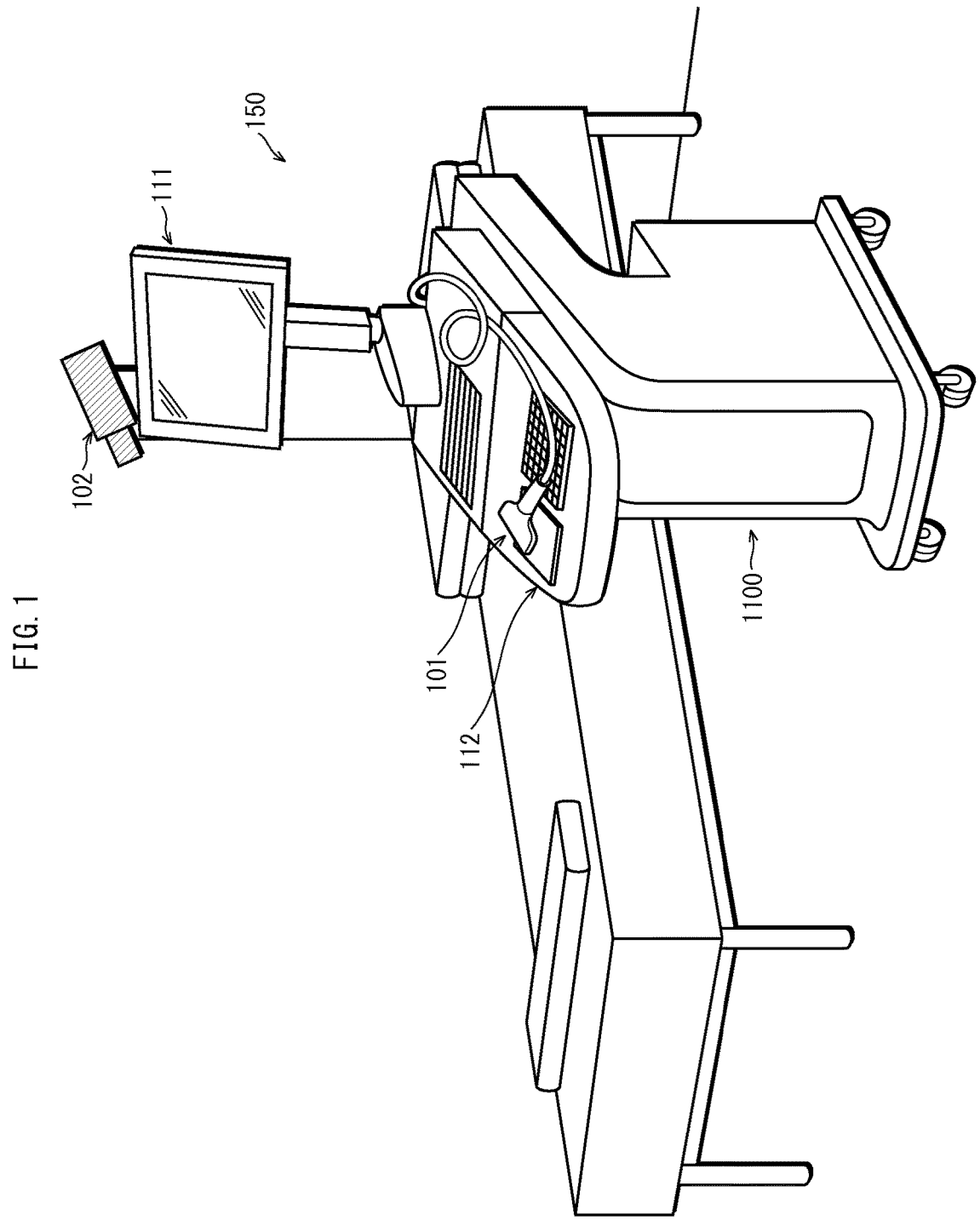
FIG. 1 illustrates an external view of an ultrasound diagnostic system 100 in which an ultrasound diagnostic apparatus 150 pertaining to Embodiment 1 is included.

The following describes embodiments the present disclosure.

Overview of Embodiments

One aspect of the present disclosure is an ultrasound diagnostic apparatus that is connectable to a probe, an imaging device, a recording medium, and a display device, and that obtains and displays ultrasound images of inside a subject's body by transmitting ultrasound towards the subject's body via the probe and receiving reflected ultrasound, the ultrasound diagnostic apparatus comprising image processing circuitry that includes: an ultrasound image generator that generates a sequence of first ultrasound images from the reflected ultrasound; a video image acquirer that acquires, from the imaging device, a sequence of first video images that captures manipulation of the probe performed during generation of the sequence of first ultrasound images; a relational recorder that records, onto the recording medium, the sequence of first ultrasound images supplied from the ultrasound image generator and the sequence of first video images supplied from the video image acquirer, in association with each other; a data reader that reads a sequence of second ultrasound images and a sequence of second video images from the recording medium, the sequence of second ultrasound images being images generated by the ultrasound image generator and recorded onto the recording medium in the past, and the sequence of second video images being video images that capture manipulation of the probe performed during generation of the sequence of second ultrasound images; and a screen composer that composes a screen by arranging the sequence of first ultrasound images, the sequence of second ultrasound images, and the sequence of second video images, and displays the screen on the display device.

The screen composer may compose the screen by additionally arranging the sequence of first video images.

The image processing circuitry may further include a video analyzer that analyzes the sequence of first video images supplied from the video image acquirer to identify an examination target part of the subject's body, and generates first examination target part identification information indicating the examination target part so identified. The relational recorder may additionally record, onto the recording medium, the first examination target part identification information in association with the sequence of first ultrasound images and the sequence of first video images. The data reader may read, from the recording medium, a pair of a sequence of second ultrasound images and a sequence of second video images that is associated with second examination target part identification information that matches the first examination target part identification information, the sequence of second ultrasound images being images generated by the ultrasound image generator and recorded onto the recording medium in the past, and the sequence of second video images being video images that capture manipulation of the probe performed during generation of the sequence of second ultrasound images.

The recording medium may store thereon body mark images. The data reader may read, from among the body mark images stored on the recording medium, a body mark image corresponding to the second examination target part identification information. The screen composer may compose the screen by additionally arranging the body mark image corresponding to the second examination target part identification information.

Another aspect of the present disclosure is an ultrasound image processing method used in an ultrasound diagnostic apparatus that is connectable to a probe, an imaging device, a recording medium, and a display device, and that obtains and displays ultrasound images of inside a subject's body by transmitting ultrasound towards the subject's body via the probe and receiving reflected ultrasound, comprising: generating a sequence of first ultrasound images from the reflected ultrasound; acquiring, from the imaging device, a sequence of first video images that captures manipulation of the probe performed during generation of the sequence of first ultrasound images; recording, onto the recording medium, the sequence of first ultrasound images and the sequence of first video images, in association with each other; reading a sequence of second ultrasound images and a sequence of second video images from the recording medium, the sequence of second ultrasound images being images generated and recorded onto the recording medium in the past, and the sequence of second video images being video images that capture manipulation of the probe performed during generation of the sequence of second ultrasound images; and composing a screen by arranging the sequence of first ultrasound images, the sequence of second ultrasound images, and the sequence of second video images, and displaying the screen on the display device.

Yet another aspect of the present disclosure is a non-transitory computer readable recording medium on which is recorded a program for causing a computer to perform the ultrasound image processing method described above.

Embodiment 1

The following explains, with reference to the drawings, an ultrasound diagnostic system 100 including an ultrasound diagnostic apparatus 150 pertaining to Embodiment 1.

<Overall Configuration of Ultrasound Diagnostic System>

Figure 2:
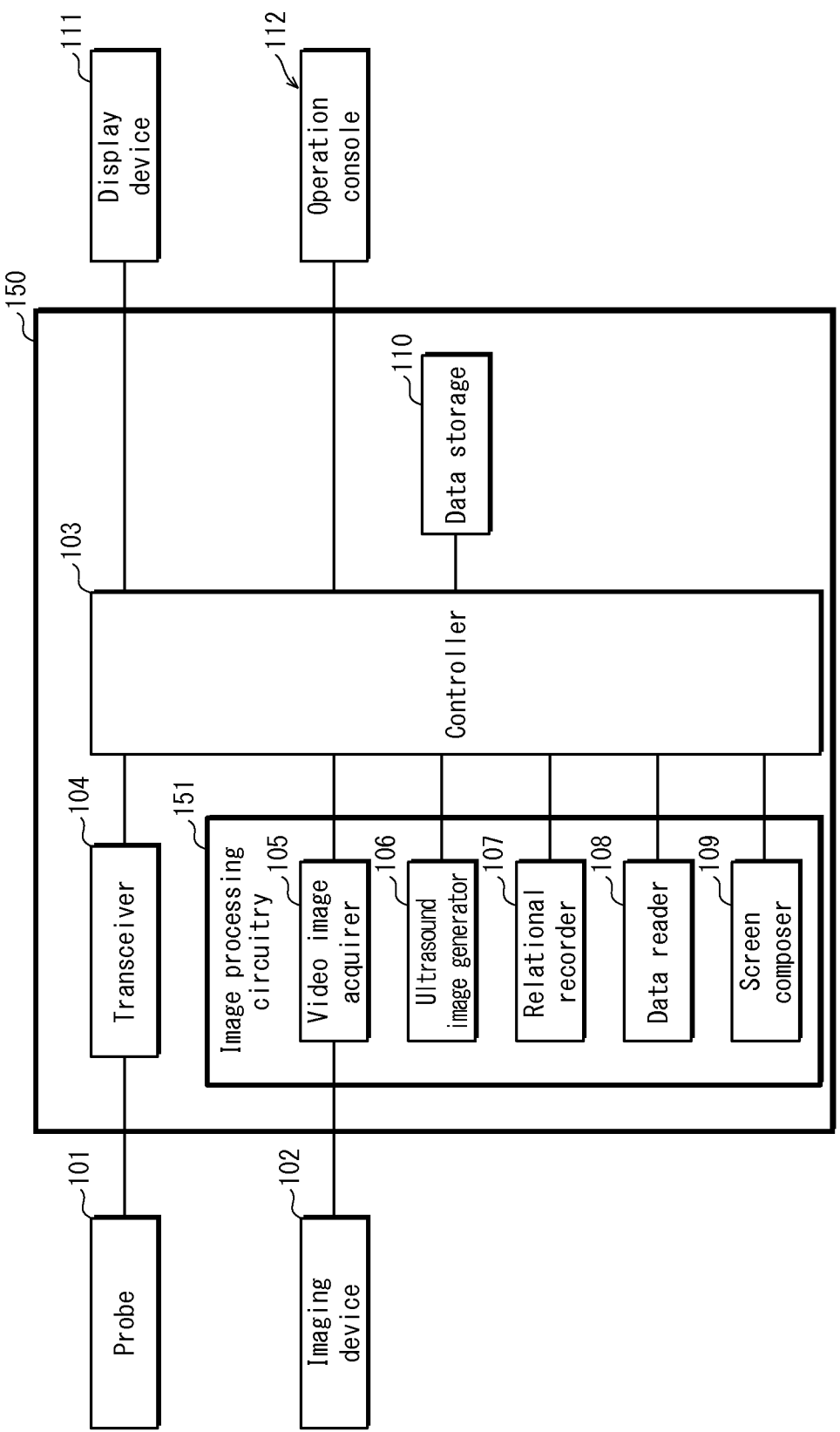
FIG. 2 is a block diagram illustrating configuration of the ultrasound diagnostic system 100 using the ultrasound diagnostic apparatus 150 pertaining to Embodiment 1.

The following describes the overall configuration of the ultrasound diagnostic system 100 including the ultrasound diagnostic apparatus 150 pertaining to Embodiment 1. The ultrasound diagnostic system 100 performs transmission and reception of ultrasound signals for ultrasound diagnosis via a probe 101, and forms images from reflected ultrasound signals so received. FIG. 1 illustrates an external view of the ultrasound diagnostic system 100 in which the ultrasound diagnostic apparatus 150 pertaining to Embodiment 1 is included. FIG. 2 is a block diagram illustrating configuration of the ultrasound diagnostic apparatus 150.

As shown in FIG. 1 and FIG. 2, the ultrasound diagnostic system 100 includes the ultrasound diagnostic apparatus 150, the probe 101, an imaging device 102, a display device 111, and an operation console 112.

The following explains each device included in the ultrasound diagnostic system 1000.

As shown in FIG. 2, the ultrasound diagnostic apparatus 150 includes a controller 103, a transceiver 104, a video image acquirer 105, an ultrasound image generator 106, a relational recorder 107, a data reader 108, a screen composer 109, and a data storage 110. Among these elements, the video image acquirer 105, the ultrasound image generator 106, the relational recorder 107, the data reader 108, and the screen composer 109 constitute image processing circuitry 151 of the ultrasound diagnostic apparatus 150.

1. Ultrasound Diagnostic Apparatus 150

Each of the elements constituting the ultrasound diagnostic apparatus 150, such as the controller 103, the transceiver 104, the video image acquirer 105, the ultrasound image generator 106, the relational recorder 107, the data reader 108, the screen composer 109 and the data storage 110, is implemented as a hardware circuit, such as field programmable gate array (FPGA) or an application specific integrated circuit (ASIC). Alternatively, each element may be implemented as a combination of programmable device, such as a central processing unit (CPU) or a processor, with software. Each of the aforementioned elements may be a single circuit component or may be a collection of circuit components. Further alternatively, a plurality of the aforementioned elements may be combined as a single circuit component or as a collection of circuit components.

The probe 101, the imaging device 102, the display device 111 and the operation console 112 are provided outside the ultrasound diagnostic apparatus 150 so as to be connectable to the ultrasound diagnostic apparatus 150. FIG. 2 shows that the probe 101, the imaging device 102, the display device 111 and the operation console 112 are connected to the ultrasound diagnostic apparatus 150. The probe 101 and the display device 111 may be included in the ultrasound diagnostic apparatus 150.

The following explains configuration of each of the elements connected externally to the ultrasound diagnostic apparatus 150.

2. Probe 101

The probe 101 has ultrasound transducers that transmit and receive ultrasound. The probe 101 has a plurality of transducers (not illustrated) arranged one-dimensionally, for example. The probe 101 converts an electrical signal pulse from the transceiver 104, which is described below, to an ultrasound pulse. The probe 101 emits a plurality of ultrasound beams from the plurality of transducers towards the subject, with the outer surfaces of the transducers of the probe 101 being in contact with the skin surface of the subject. The probe 101 receives a plurality of reflected ultrasound waves (hereinafter, "reflected ultrasound signals") as echo signals from the subject, converts the reflected ultrasound signals to electrical signals (hereinafter, "reception signals") by using the plurality of transducers, and provides the reception signals to the transceiver 104.

3. Imaging Device 102

The imaging device 102 is a camera that captures manipulation of the probe 101 during the examination, according to instructions from the controller 103, and sequentially outputs video image signals to the video image acquirer 105. In the ultrasound diagnostic apparatus 150, the imaging device 102 sequentially outputs image signals to the video image acquirer 105 while the imaging device 102 is being supplied with electricity.

The imaging device 102 is for example a video camera as shown in FIG. 1, and forms an image onto an imaging element (e.g. CCD or CMOS) by collecting light thereon by using a lens, and converts the light to electrical signals. The imaging device 102 is mounted and fixed on the upper part of the display device 111 for example, and is orientated such that the lens barrel faces towards where an examination target part is usually positioned. The controller 103 outputs control signals to the imaging device 102 via the video image acquirer 105 according to instructions input by the examiner from the operation console 112, and the imaging device 102 performs adjustment operations according to the control signals. The control signals control the angle of the lens barrel, zoom conditions, focal conditions, etc. Thus the examiner can control the angle of the lens barrel, zoom conditions, focal conditions, etc. of the imaging device 102 in order to face the imaging device 102 towards the examination target part of the subject by inputting instructions from the operation console 112. More specifically, the examiner can control the angle of the lens barrel, zoom conditions, focal conditions, etc. of the imaging device 102 by inputting instructions from the operation console 112 while viewing the video images from the imaging device 102 displayed on the display screen. The video image acquirer 105 records information related to the conditions of imaging, such as the angle of the lens barrel and zoom and focal conditions, into, for example, the header of the file of captured video images. The sequence of video images with this information is written into the data storage 110 by the video image acquirer 105. Therefore, the imaging device 102 can capture the video images of the examination target part of the subject under the same conditions as the video images captured in the past, by reproducing the information related to the conditions of imaging, recorded in the header of the video file.

Note that a plurality of imaging devices 102 may be provided. By switching between a plurality of imaging devices 102 each corresponding to one examination target part, the examiner can view a desired part without changing the angle of the lens barrel and the zoom and focal conditions each time when the part to be examined is changed. Furthermore, the video image acquirer 105 may combine the image signals received from each of the plurality of imaging devices 102, thereby generating video images that provide a sense of depth. Such video images enable the examiner to know more precise movement of the examination target part of the subject and precise manipulation of probe performed during the acquisition of the ultrasound images.

3. Display Device 111

The display device 111 is a device that displays images. The display device 111 displays a sequence of reference video images, a sequence of reference ultrasound images, video images that are currently being acquired (hereinafter, "current video images"), and a sequence of ultrasound images that are currently being acquired (hereinafter, "current ultrasound images"), which are output via the controller 103 described below, according to screen composition determined by the screen composer 109. The display device 111 is implemented as a liquid crystal display (LCD) or an organic EL display, for example.

4. Operation Console 112

The operation console 112 is an input device, and receives various sorts of information related to the settings of the ultrasound diagnostic apparatus 150 and operations of the ultrasound diagnostic apparatus 150 from the examiner, and outputs the instructions to the controller 103. The information input by the examiner relates to, for example, a patient name, an examination date, operation or suspension of a screen, storage, and image quality adjustment. The input information is written into the data storage 110.

The operation console 112 may for example be a keyboard, a trackball, or a touch panel. If the operation console 112 is a touch panel, the operation console 112 may be integrated with the display device 111. In such a configuration, the ultrasound diagnostic apparatus 150 can be operated using the touch panel by performing an operation, such as a touch operation or a drag operation, with respect to an operation key displayed on the display device 111, in order to perform a setting or an operation with respect to the ultrasound diagnostic apparatus 150.

The operation console 112 may alternatively be a keyboard that has keys for performing various operations, or may be an operation panel that has buttons, levers, or the like for performing various operations. Further alternatively, the operation console 112 may be a trackball, a mouse, or any other equipment for moving a cursor displayed on the display device 111. Note that the operation console 112 may alternatively be a plurality of any of the aforementioned types of equipment, or may be a combination of different types of the aforementioned equipment.

<Configuration of Elements of Ultrasound Diagnostic Apparatus 150>

The following explains configuration of each of the functional blocks included in the ultrasound diagnostic apparatus 150.

1. Controller 103

The controller 103 controls each processing element included in the ultrasound diagnostic apparatus 150. Hereinafter, although no special description is given, the controller 103 is the circuit that controls operations of each processing element. For example, the controller 103 causes each processing element to perform processing while controlling operation timing and so on.

2. Transceiver 104

The transceiver 104 is connected to the probe 101. The transceiver 104 is circuitry that performs transmission processing according to transmission control signals from the controller 103 in order to supply the probe 101 with a transmission ultrasound signal pulse, which enables the probe 101 to transmit an ultrasound beam. Specifically, the transceiver 104 includes a clock generation circuit, a pulse generation circuit, and delay circuit, for example. The clock generation circuit is a circuit that generates a clock signal used for determining transmission timing of the ultrasound beam. The pulse generation circuit is a circuit that generates a pulse signal for driving each of the transducers. The delay circuit is a circuit for performing ultrasound beamforming or ultrasound beam-steering by setting a delay time for ultrasound beam transmission with respect to each of the transducers and delaying ultrasound beam transmission from each of the transducers by the delay time set with respect thereto.

The transceiver 104 also serves as circuitry by which the reception ultrasound signal based on the reflected ultrasound, acquired by the probe 101 is amplified and AD converted to an RF signal, and delay-and-sum is performed on the RF signal to generate the acoustic signal along the depth direction. The transceiver 104 also performs a reception process of outputting an acoustic signal to the ultrasound image generator 106 and the video image acquirer 105 in the order of ultrasound scanning.

The RF signal is for example formed from a plurality of signals in the transducer arrangement direction and in an ultrasound transmission direction perpendicular thereto, wherein each of the signals is an amplitude converted electrical signal of reflected ultrasound that is A/D converted to a digital signal.

The acoustic signal is continuous data in the depth direction configuring the RF signal after the delay-and-sum process has been performed thereon. The depth direction is a direction in which a transmission ultrasound signal travels from the surface of a body of a subject toward the inside of the body of the subject. The acoustic signal is for example formed from a plurality of frames in the transducer arrangement direction and in an ultrasound transmission direction perpendicular thereto. An acoustic signal acquired through a single ultrasound scan is referred to as a frame acoustic signal. The term "frame" is used to express a unit of a group of signals necessary in order to construct a single ultrasound image.

The transceiver 104 successively repeats the transmission process and the reception process.

3. Image Processing Circuitry 151

Figure 3:
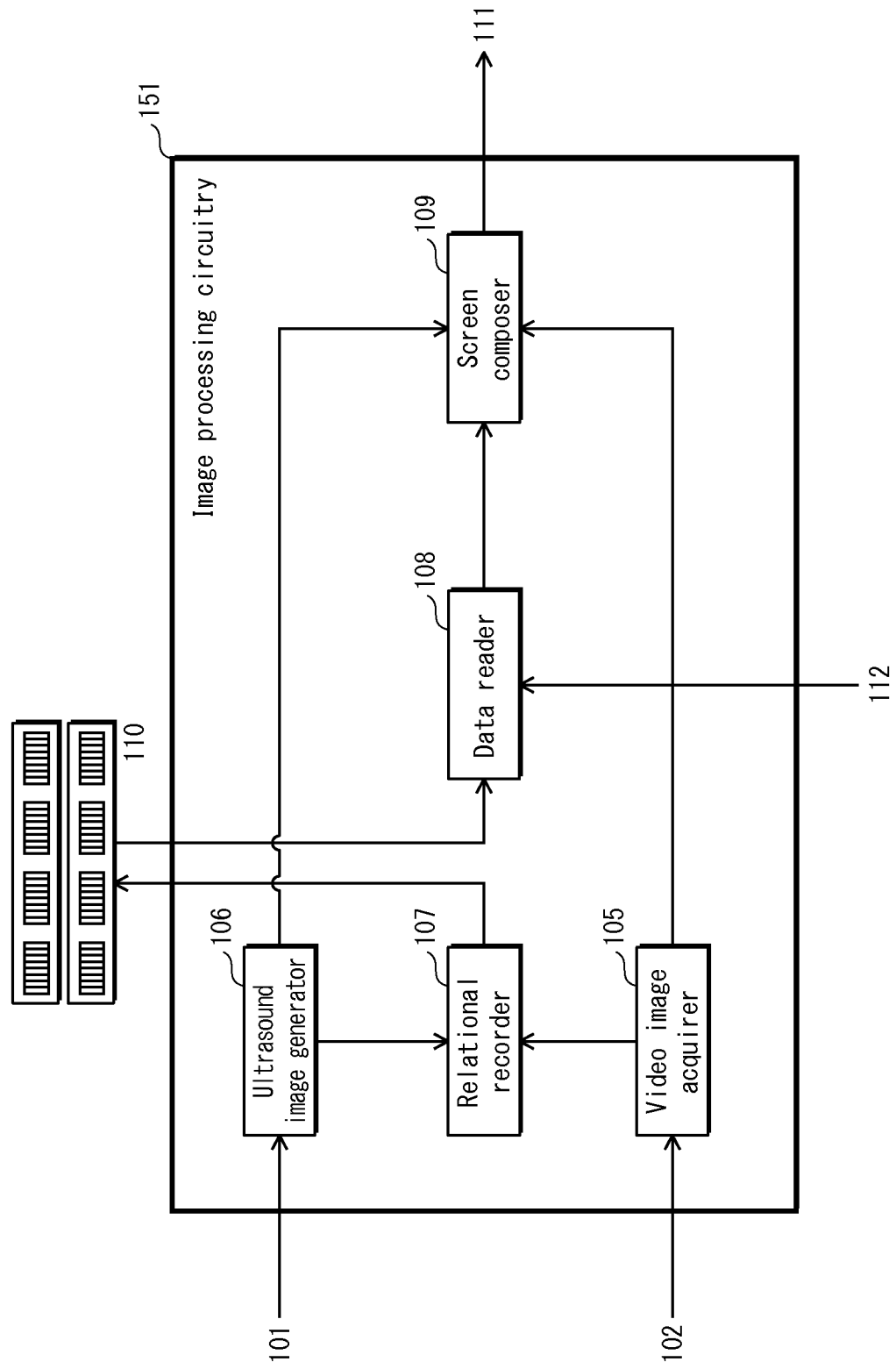
FIG. 3 is a block diagram illustrating configuration of image processing circuitry 151 of the ultrasound diagnostic apparatus 150.

The following explains configuration of the image processing circuitry 151 of the ultrasound diagnostic apparatus 150 pertaining to Embodiment 1. FIG. 3 is a block diagram illustrating the configuration of the image processing circuitry 151 of the ultrasound diagnostic apparatus 150. As described above, the image processing circuitry 151 of the ultrasound diagnostic apparatus 150 includes a video image acquirer 105, the ultrasound image generator 106, the relational recorder 107, the data reader 108, and the screen composer 109.

(1) Video Image Acquirer 105

The video image acquirer 105 acquires video images captured by the imaging device 102. The video image acquirer 105 is a circuit that receives image signals sequentially output by the imaging device 102, thereby acquiring video images that capture the manipulation of the probe manipulated by the examiner. The video image acquirer 105 starts or stops acquiring video images according to control signals received from the controller 103.

The video image acquirer 105 is controlled by the controller 103 so as to start or stop acquiring the video images in synchronization with the start and stop of the transmission and reception of ultrasound. Specifically, when the examiner inputs a freeze cancellation instruction from the operation console 112, the controller 103 outputs a control signal for starting the transmission and reception processing to the transceiver 104, and at the same time, outputs a control signal for starting the acquisition of the video images to the video image acquirer 105. Accordingly, the transmission and reception processing of the transceiver 104 and the video image acquisition by the video image acquirer 105 are started at the same time. On the other hand, when the examiner inputs a freeze instruction from the operation console 112, the controller 103 outputs a control signal for stopping the transmission and reception processing to the transceiver 104, and at the same time, outputs a control signal for stopping the acquisition of the video images to the video image acquirer 105. Accordingly, the transmission and reception processing of the transceiver 104 and the video image acquisition by the video image acquirer 105 are stopped at the same time.

The video images acquired by the video image acquirer 105 are output to the data storage 110 via the controller 103 and is stored therein.

(2) Ultrasound Image Generator 106

The ultrasound image generator 106 is a circuit that generates ultrasound images based on reflected ultrasound from the subject acquired by the probe 101. The ultrasound images are B-mode ultrasound images in which the strength of an ultrasound reception signal is expressed by luminance. The following explains a case where the examiner acquires reflected ultrasound while moving the probe on the subject. Note that the probe is not necessarily moved along a straight line. That is, the following explanation is applicable to the case where the examiner moves the probe along a curved line.

The ultrasound image generator 106 generates an ultrasound image as a single frame by converting each acoustic signal of each frame into a luminance signal corresponding to strength of the acoustic signal, and by subsequently performing coordinate conversion on the luminance signal to an orthogonal coordinate system. The ultrasound image generator 106 sequentially performs this processing for each frame, and outputs the generated ultrasound images to the data storage 110 via the controller 103. Specifically, the ultrasound image generator 106 performs filter processing on reflected ultrasound, and then performs envelope detection. Furthermore, the ultrasound image generator 106 performs logarithmic conversion and gain control on a signal resulting from the envelope detection, thereby generating ultrasound images. The ultrasound images as frames generated by the ultrasound image generator 106 are sequentially stored in the data storage 110 each time ultrasound scan is performed. Note that the ultrasound image generator 106 may sequentially generate the ultrasound images. The sequence of ultrasound images may be recorded as a sequence of cross-sectional video images.

(3) Relational Recorder 107

The relational recorder 107 is a circuit that records ultrasound images and video images into the data storage 110 in association with each other. The ultrasound diagnostic apparatus 150 generates a storage data list showing the correlation between the ultrasound images and the video images, and stores the list into the data storage 110. In the present embodiment, the correlation between the ultrasound images and the video images is recorded in units of files. Specifically, as shown in FIG. 3, the relational recorder 107 receives a sequence of ultrasound images that is currently being acquired by the ultrasound image generator 106, and a sequence of video images that is currently being acquired by the video image acquirer 105, and stores the sequence of ultrasound images and the sequence of video images as separated files of reference images onto the data storage 110. The relational recorder 107 also updates the storage data list by writing an additional information set into the storage data list stored in the data storage 110. The additional information set indicates the correlation between the sequence of ultrasound images and the sequence of video images. Thus the storage data list stored in the data storage 110 is updated each time a new set of ultrasound images is acquired by the ultrasound image generator 106, with an additional information set added to the storage data list each time.

FIG. 4 is a schematic diagram illustrating an example of a storage data list which is output by the relational recorder 107. The storage data list according to the present embodiment is a list of data items each including a subject ID, a time stamp showing an examination date, information of a link to a sequence of video images, and information of a link to a sequence of ultrasound images. The correlation between the sequence of ultrasound images and the sequence of video images is established by recording the information of the link to the sequence of ultrasound images and the link to the sequence of video images into the storage data list in this way. Thus a sequence of ultrasound images as frames and a sequence of video images as frames can be associated with each other by the storage data list and then recorded in the data storage 110.

Note that the relational recorder 107 may associate the ultrasound images and the video images with each other on a frame-to-frame basis. If this is the case, an additional information set is generated for each pair of an ultrasound image as a frame and a video image as a frame, and is recorded into the storage data list stored in the data storage 110.

In the above-described embodiment, the storage data list is used for associating ultrasound images and video images. However, any other method may be used insofar as it can associate ultrasound images and video images in one-to-one correspondence. For example, information of a video file may be added to, for example, the header of an ultrasound image file, and file information of the ultrasound image file may be added to, for example, the header of the video file.

(4) Data Reader 108

The data reader 108 is a circuit that reads a sequence of ultrasound images and a sequence of video images which are associated with each other (hereinafter, collectively referred to as "reference images") in response to an operational instruction input from operation console 112 by the examiner. The examiner can select and view a desired ultrasound image by inputting an instruction from the operation console 112 while viewing the screen showing a patient's electronic medical records for example. When the examiner selects a sequence of ultrasound images from the operation console 112, a sequence of video images corresponding to the ultrasound images is simultaneously read from the data storage 110. At this stage, the storage data list may be used for enabling the user to select a sequence of ultrasound images. With this configuration, the examiner can narrow down the list of selectable ultrasound images by specifying a subject ID, an examination date, and so on, and then select a sequence of ultrasound images. Note that the data reader 108 may be configured to read ultrasound images corresponding to a sequence of video images selected by the examiner. Any method may be used insofar as it allows for reading selected ultrasound images and video images corresponding to the ultrasound images.

(5) Screen Composer 109

The screen composer 109 is a circuit that composes a screen by arranging the sequence of reference images (i.e. ultrasound images selected by the examiner and the video images corresponding to the ultrasound images) and the data currently being acquired (e.g. the sequence of ultrasound images that are currently being generated by the ultrasound image generator 106), and displays the screen on the display device 111. Note that the data currently being acquired may include also a sequence of video images acquired by the video image acquirer. Note that the term "arrange" does not limit the positional relationship among the reference images and the images currently being acquired. The essential point is that the reference images and the ultrasound images (and the video images) currently being acquired are positioned within the screen.

Specifically, as shown in FIG. 3, the screen composer 109 composes a screen to be displayed on the display device 111, by arranging the reference images read by the data reader 108 from the data storage 110, namely a sequence of ultrasound images and a sequence of video images associated with each other, and a sequence of ultrasound images that are currently being acquired and supplied directly from the ultrasound image generator 106. The screen composer 109 outputs image signals constituting the screen to the display device 111 via the controller 103. The screen composer 109 may compose the screen by arranging additionally the sequence of video images that are currently being acquired and supplied directly from the video image acquirer 105.

4. Data Storage 110

The data storage 110 is a recording medium that stores therein ultrasound images generated by the ultrasound image generator 106, video images acquired by the video image acquirer 105, correlation information such as a storage data list generated by the relational recorder 107, information of a screen composed by the screen composer 109, and operational instructions input from the operation console 112, for example, which are input to the data storage 110 via the controller 103. The data storage 110 is a computer readable recording medium, which can be implemented as a flexible disk, hard disk, MO, DVD, DVD-RAM or semiconductor memory, for example. The data storage 110 may be a storage device that is externally connected to the ultrasound diagnostic apparatus 150.

<Images Contained in Screen>

The following explains an example of a screen displayed by the ultrasound diagnostic apparatus 150. Each of FIGS. 6, 7 and 8 illustrates an example of a screen displayed by the ultrasound diagnostic apparatus 150.

Figure 6:
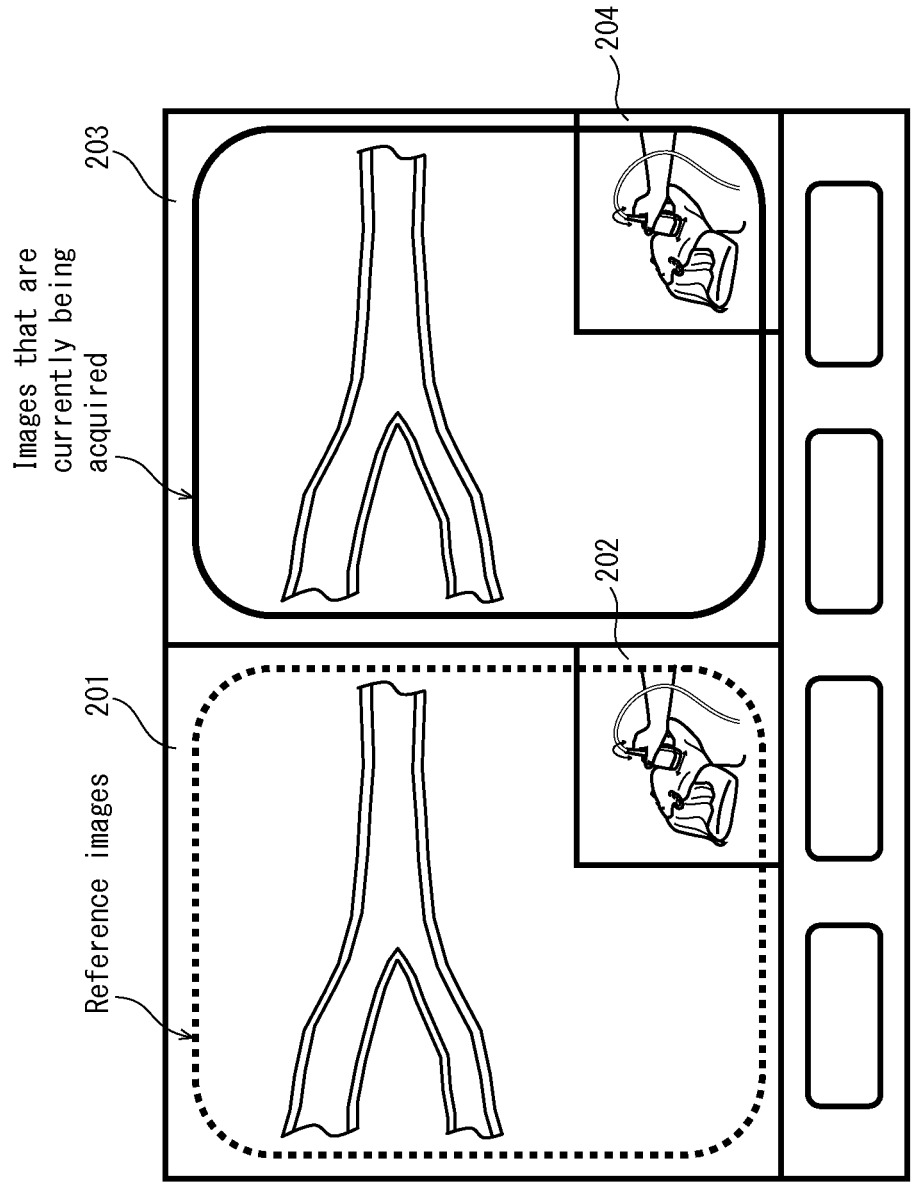
FIG. 6 is a schematic diagram illustrating an example of a screen displayed by the ultrasound diagnostic apparatus 150.
Figure 7:
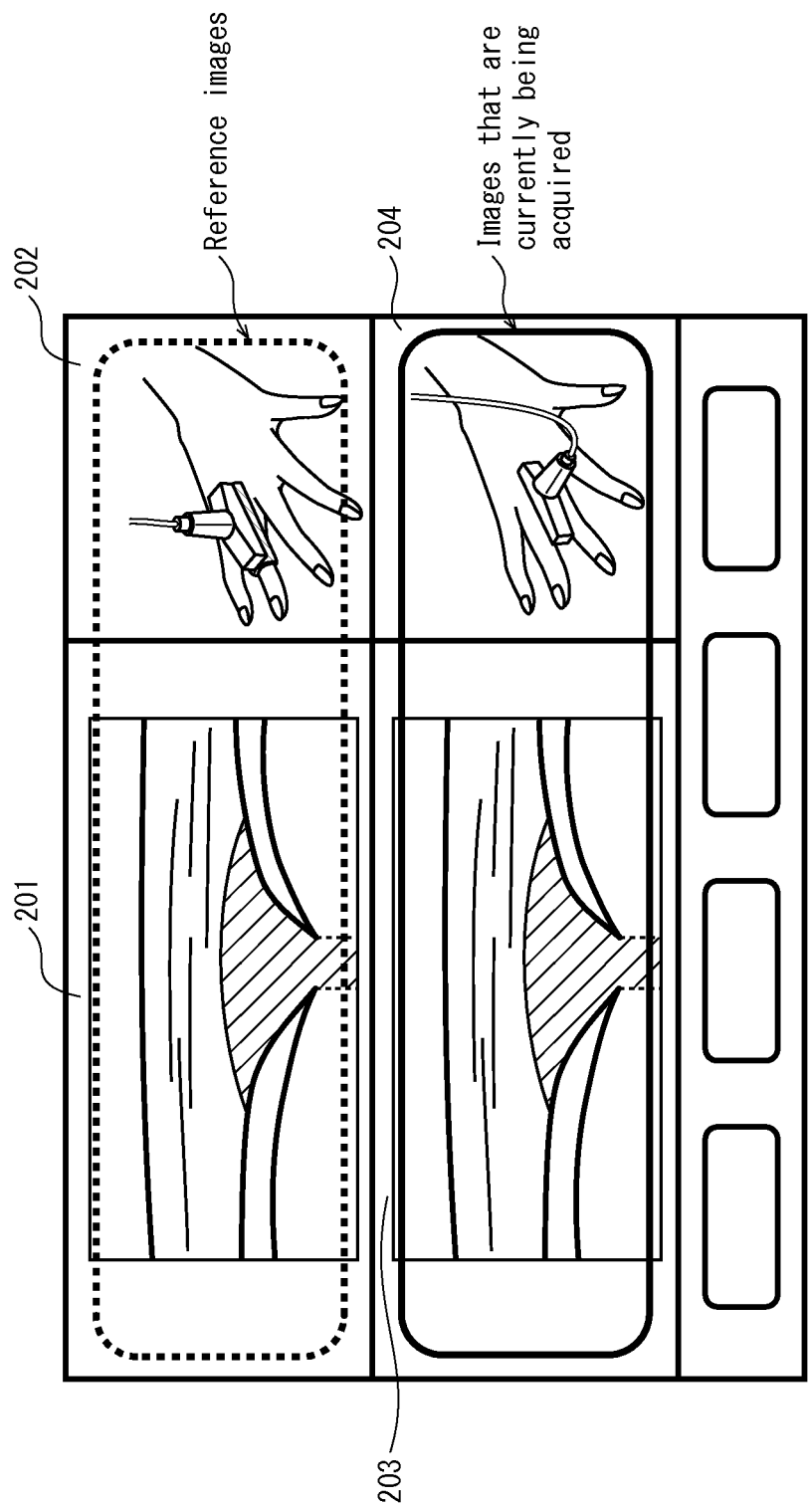
FIG. 7 is a schematic diagram illustrating another example of the screen displayed by the ultrasound diagnostic apparatus 150.
Figure 8:
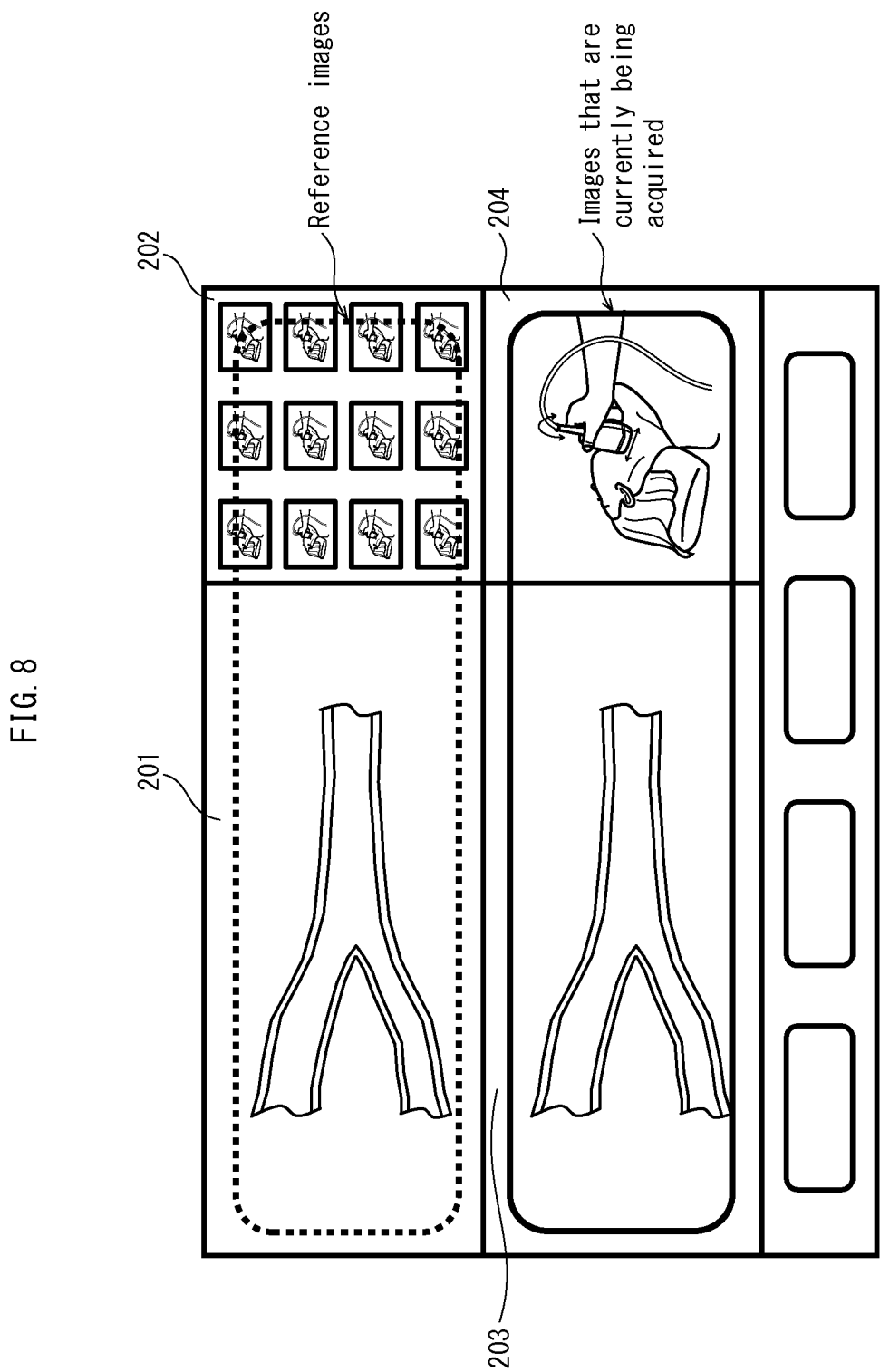
FIG. 8 is a schematic diagram illustrating another example of the screen displayed by the ultrasound diagnostic apparatus 150.

As shown in FIG. 6, FIG. 7 and FIG. 8, the screen composed by the screen composer 109 contains the reference images, and the ultrasound images and video images that are currently being acquired. The screen in which these images are arranged is displayed on the display device 111. In the case of the example shown in FIG. 6, the screen composer 109 composes a screen by arranging reference ultrasound images within a window 201, reference video images within a window 202, current ultrasound images within a window 203, and current video images within a window 204.

Such a screen enables the examiner to perform an ultrasound examination while checking the movement of the examination target part of the subject and the manipulation of the probe that were performed during the acquisition of the reference ultrasound images. Also, the screen enables the examiner to reproduce the same situation shown by the reference images by performing examination while moving the subject or the probe with reference to the reference images. Accordingly, the examiner can compare the current images and the reference images under the same conditions, which leads to more accurate diagnosis.

The configuration of the screen is not limited to the configuration shown in FIG. 6. Any configuration may be adopted insofar as it enables the examiner to compare the reference ultrasound images with current ultrasound images, and reference video images with current video images. For example, the configuration shown in FIG. 7 may be adopted. According to this configuration, the reference ultrasound images are located within the window 201, the reference video images are located within the window 202, the current ultrasound images are located within the window 203, and the current video images are located within the window 204. This configuration of the screen is useful particularly for a surface layer examination, such as an orthopedic ultrasound examination for finger joints. More specifically, the windows 201 and 203 of this screen have an horizontally elongated shape, and the screen shows the reference images and the current images located one above the other. Such a configuration makes it easy to compare the inner tissues extending along the body surface.

Alternatively, as shown in FIG. 8, the reference video images may be displayed as thumbnails. According to this configuration, the reference ultrasound images are located within the window 201, the reference video images are located within the window 202, the current ultrasound images are located within the window 203, and the current video images are located within the window 204. In addition, the reference video images shown in the window 202 are arranged in the form of thumbnails each corresponding to one of the frames of the video. This configuration enables the examiner to browse the sequence of movement of the subject and manipulation of the probe performed during the acquisition of the reference images, and makes it easy to acquire precise information of the examination performed during the acquisition of the reference images.

<Operations>

Figure 5:
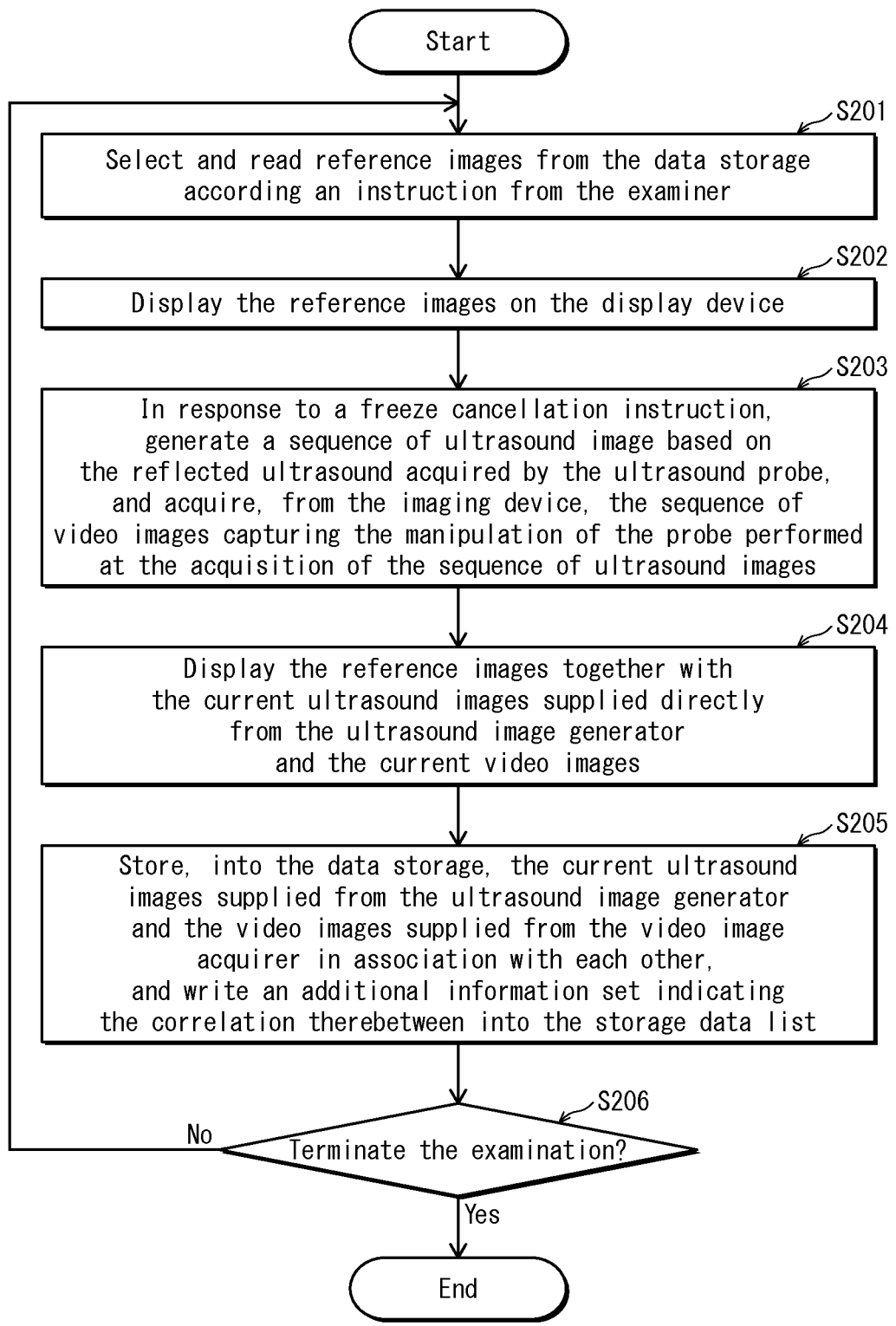
FIG. 5 is a flowchart illustrating example operations for ultrasound image display processing performed by the ultrasound diagnostic apparatus 150.

Operations of the ultrasound diagnostic apparatus 150 pertaining to Embodiment 1 are described below. FIG. 5 is a flowchart illustrating example operations for ultrasound image display processing performed by the ultrasound diagnostic apparatus 150.

1. Step S201

At Step S201, the data reader 108 selects, from among a plurality of sequences of reference images (i.e. reference ultrasound images and reference video images) stored in the data storage 110, a sequence of reference images, according to an instruction input from the operation console 112 by the examiner, and the screen composer 109 reads the selected reference images from the data storage 110. As described above, the data storage 110 stores, as reference images, sequences of ultrasound images and sequences of video images in one-to-one correspondence. Therefore, when one sequence of ultrasound images is selected, the sequence of video images capturing the manipulation of the probe performed by the examiner during the acquisition of the sequence of ultrasound images is also read from the data storage 110.

Note that the operations illustrated in FIG. 5 are performed repeatedly, and the above-described process of recording the correlation between the ultrasound images and the video images corresponds to Step S205 described below. Thus at Step S201, the ultrasound images and video images recorded in the past are treated as reference images.

2. Step S202

At Step S202, the screen composer 109 displays the reference images read at Step S201 on the display device 111. Note that the screen composer 109 composes the screen by arranging the reference ultrasound images and video images within the window 201 as shown in FIG. 6, FIG. 7 or FIG. 8 for example. Playback of the ultrasound images and playback of the video images are started automatically. The ultrasound images and the video images are played back in synchronization. That is, an ultrasound image and a video image acquired at the same point of time are displayed at the same time. Accordingly, the examiner can know the manipulation of the probe performed during the acquisition of the reference ultrasound images (i.e. how the examination was performed during the acquisition of the reference ultrasound images).

3. Step S203

At Step S203, an ultrasound examination is started according to an instruction from the examiner. That is, according to a freeze cancellation instruction input by the examiner from the operation console 112, transmission and reception of ultrasound by the transceiver 104 is started, and the ultrasound image generator 106 generates a sequence of ultrasound images based on reflected ultrasound acquired by the probe 101. Simultaneously, the video image acquirer 105 starts acquiring a sequence of video images that is acquired by the imaging device 102 and captures the manipulation of the probe performed during the acquisition of the ultrasound images.

The examiner performs an ultrasound examination by operating the probe 101 to acquire ultrasound images inside the subject's body. Preferably, the examiner moves the probe 101 to attach the probe 101 to the examination target part of the subject by following the manipulation shown by the reference video images displayed on the screen of the display device 111.

4. Step S204

At Step S204, the screen composer 109 displays, on the display device 111, a screen composed from current ultrasound images that are supplied directly from the ultrasound image generator 106 and current video images that are supplied directly from the video image acquirer 105. The screen composer displays the current ultrasound images and video images within the window 202 shown in FIG. 6, FIG. 7 or FIG. 8 for example.

Since the screen composer 109 already started displaying the reference images read from the data storage 110 at Step S202, the current ultrasound images and current video images are displayed together with the reference images on the display device 111.

The examiner operates the probe 101 such that current video images match the reference video images, thereby acquiring new ultrasound images, and performs a comparison examination using the reference ultrasound images and the current ultrasound images. In other words, by comparing the current video images with the reference video images on the screen displayed on the display device 111, the examiner attaches the probe 101 to the examination target part of the subject such that the positional relationship between the examination target part and the probe 101 in the current video images will be the same as in the reference video images.

Generally, ultrasound diagnostic apparatuses provide, in real time, video images showing the state of tissues inside the body. Therefore, ultrasound diagnostic apparatuses are often used in an orthopedic examination, in which the dynamic state of the inside tissues of a target part such as a sinew or a join is examined while moving the part. In such an examination, it is difficult to know exactly how the examination was performed from ultrasound images inside the examination target part and still images showing the probe and the examination target part, because neither the temporal relationship between the images or the movement of the examination target part and the manipulation of the probe can be seen from the images.

In contrast, the ultrasound diagnostic apparatus 150 displays reference video images that capture the manipulation of the probe performed during the acquisition of the reference ultrasound images. Therefore, the ultrasound diagnostic apparatus 150 allows the examiner to correctly know the movement of the examination target part and the manipulation of the probe before and after the ultrasound images were acquired. Thus, the ultrasound diagnostic apparatus 150 allows the examiner to reproduce the manipulation of the probe and the movement of the examination target part performed during an examination in the past, thereby realizing an ultrasound examination at a high level of accuracy and reproducibility.

Also, as already described above, the examiner attaches the probe 101 to the examination target part of the subject such that the positional relationship between the examination target part and the probe 101 in the current video images will be the same as in the reference video images. By this operation, the examiner can acquire the ultrasound images of the examination target part in the same manner as when the reference ultrasound images were acquired.

According to the ultrasound diagnostic apparatus 150, the reference video images show the manipulation of the probe performed during the acquisition of the reference ultrasound images. As already described above, the reference images and the current ultrasound images and video images, which are acquired under the same condition, are displayed together on the display device 111. Therefore, the examiner can attach the probe 101 to the examination target part of the subject such that the positional relationship between the examination target part and the probe 101 in the current video images will be the same as in the reference video images, while comparing the current video images with the reference video images, both displayed on the display device 111. Accordingly, the examiner can position the probe 101 easily and quickly such that the positional relationship between the examination target part and the probe 101 in the current video images will be the same as in the reference video images. Also, the ultrasound diagnostic apparatus 150 reduces the workload because the examiner can perform an examination by viewing only the screen displayed on the display device 111.

5. Step S205

At Step S205, the relational recorder 107 associates a sequence of current ultrasound images supplied from the ultrasound image generator 106 and a sequence of current video images supplied from the video acquirer 105 with each other, and records the current ultrasound images and the current video images into the data storage 110. Simultaneously, the relational recorder 107 creates an additional information set indicating the correlation between the ultrasound images and the video images, and updates the storage data list stored in the data storage 110 by writing the additional information set into the storage data list.

6. Step S206

At Step S206, the ultrasound examination for the examination target part according to a freeze instruction input by the examiner from the operation console 112. The transceiver 104 stops transmission and reception of ultrasound, and the video acquirer 105 stops image capturing by the imaging device 102. Simultaneously, the relational recorder 107 stops recording the correlation between the current ultrasound images and video images. The screen composer 109 stops displaying the reference images on the display device 111, which have been displayed since Step S202.

The ultrasound examination is terminated when the examiner inputs an instruction to terminate the examination from the operation console 112 (Yes at Step S206), and otherwise (No at Step S206) the process is repeated from Step S201 so that examination for another part can be performed.

<Effects>

As described above, one aspect of the present disclosure is an ultrasound diagnostic apparatus 150 comprising image processing circuitry 151 that includes: an ultrasound image generator 106 that generates a sequence of first ultrasound images from the reflected ultrasound; a video image acquirer 105 that acquires, from the imaging device 102, a sequence of first video images that captures manipulation of the probe 101 performed during generation of the sequence of first ultrasound images; a relational recorder 107 that records, onto the recording medium 110, the sequence of first ultrasound images supplied from the ultrasound image generator 106 and the sequence of first video images supplied from the video image acquirer 105, in association with each other; a data reader 108 that reads a sequence of second ultrasound images and a sequence of second video images from the recording medium 110, the sequence of second ultrasound images being images generated by the ultrasound image generator 106 and recorded onto the recording medium 110 in the past, and the sequence of second video images being video images that capture manipulation of the probe 101 performed during generation of the sequence of second ultrasound images; and a screen composer 109 that composes a screen by arranging the sequence of first ultrasound images, the sequence of second ultrasound images, and the sequence of second video images, and displays the screen on the display device 111.

This configuration allows the examiner to correctly know the movement of the examination target part of the subject and the manipulation of the probe that were performed during the acquisition of the ultrasound images for comparison examination in an ultrasound examination. Therefore, in an orthopedic examination for example, when the examiner examines the dynamic state of the tissues inside the body while moving the subject's body, the examiner can reproduces the same manipulation of the probe and the same movement of the subject as in an examination performed in the past. Thus the examiner can perform an ultrasound examination at a high level of accuracy and reproducibility.

The screen composer 109 may compose the screen by additionally arranging the sequence of first video images.

This configuration allows the examiner to perform an ultrasound examination while, on the same screen, comparing the sequence of video images that captures the manipulation of the probe performed during an examination recorded in the past and the sequence of video images that captures the manipulation of the probe that is currently acquiring the sequence of ultrasound images. Therefore, the examiner can reproduce a procedure for an examination performed in the past, and accordingly the examiner can swiftly and easily perform an accurate comparison examination.

According to conventional technology, the examiner cannot see the examination target part of the subject while seeing the ultrasound images displayed on the display device. Therefore, the examiner needs to view the examination target part and the display screen alternately. In contrast, the ultrasound diagnostic apparatus 150 allows the examiner to see the examination target part in the form of video images displayed on the display device while being acquired. The examiner can perform an examination by simply seeing the video images and ultrasound images that are currently being acquired and displayed together on the display device. In this way, the ultrasound diagnostic apparatus 150 reduces the workload on the examiner.

Furthermore, as the reference images are images recorded in the past, the examiner can correctly know changes over time in tissues inside the subject's body by comparing the current ultrasound images with the reference images. This allows the examiner to make a precise decision on the effects of treatment.

Furthermore, when the reference images are ultrasound images showing healthy state and the images currently being acquired are images showing a diseased state, the examiner can perform relative evaluation as to the diseased part.

Embodiment 2

The configuration of an ultrasound diagnostic apparatus 152 pertaining to Embodiment 2 is described below. The ultrasound diagnostic apparatus 152 identifies the examination target part by analyzing the sequence of video images that capture the manipulation of the probe performed during the acquisition of the sequence of ultrasound images, and records, into the data storage, examination target part identification information that associates the examination target part with the ultrasound images. The ultrasound diagnostic apparatus 152 also has the function of specifying the reference images corresponding to the examination target part identification information from among reference images stored in the data storage, and referring to the reference images so specified.

According to the ultrasound diagnostic apparatus 150 pertaining to Embodiment 1, the examiner needs to manually select reference images by inputting an instruction from the operation console 112. However, it is troublesome to select desired reference images from among many reference images stored in the data storage 110. For example, in the case of an examination for rheumatoid arthritis, it is proposed to examine forty-four finger joints in total, and it is necessary to keep a large volume of recording data. In such a case, it is particularly troublesome to correctly select desired reference images.

In order to reduce the workload of correctly selecting desired reference images, the ultrasound diagnostic apparatus 152 pertaining to Embodiment 2 has a video image analyzer 213 that identifies the examination target part by analyzing the video images that are currently being acquired, so that the reference images corresponding to the examination target part can be automatically selected by the data reader 208.

<Overall Configuration>

Figure 9:
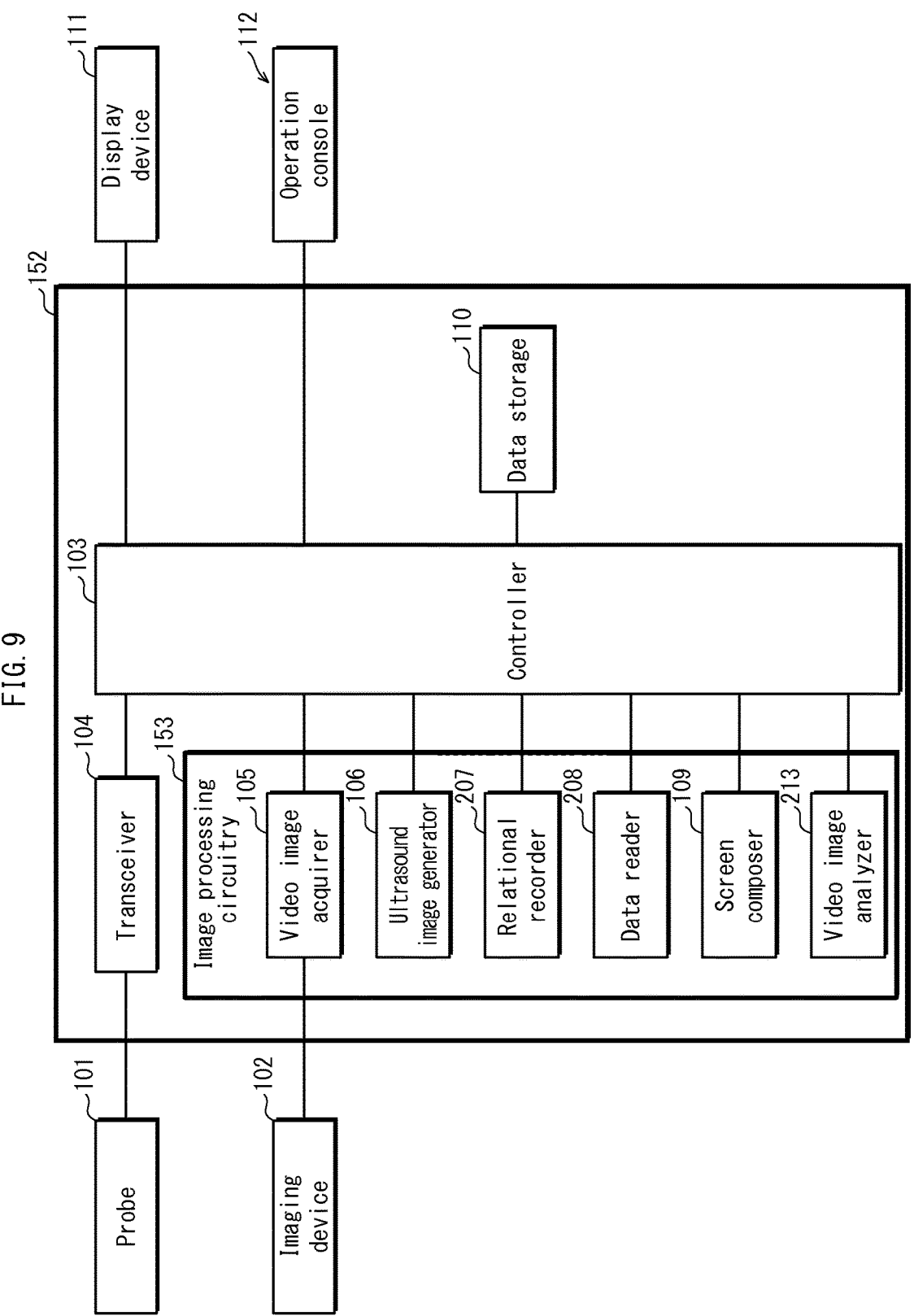
FIG. 9 is a block diagram illustrating configuration of an ultrasound diagnostic system 100 using an ultrasound diagnostic apparatus 152 pertaining to Embodiment 2.
Figure 10:
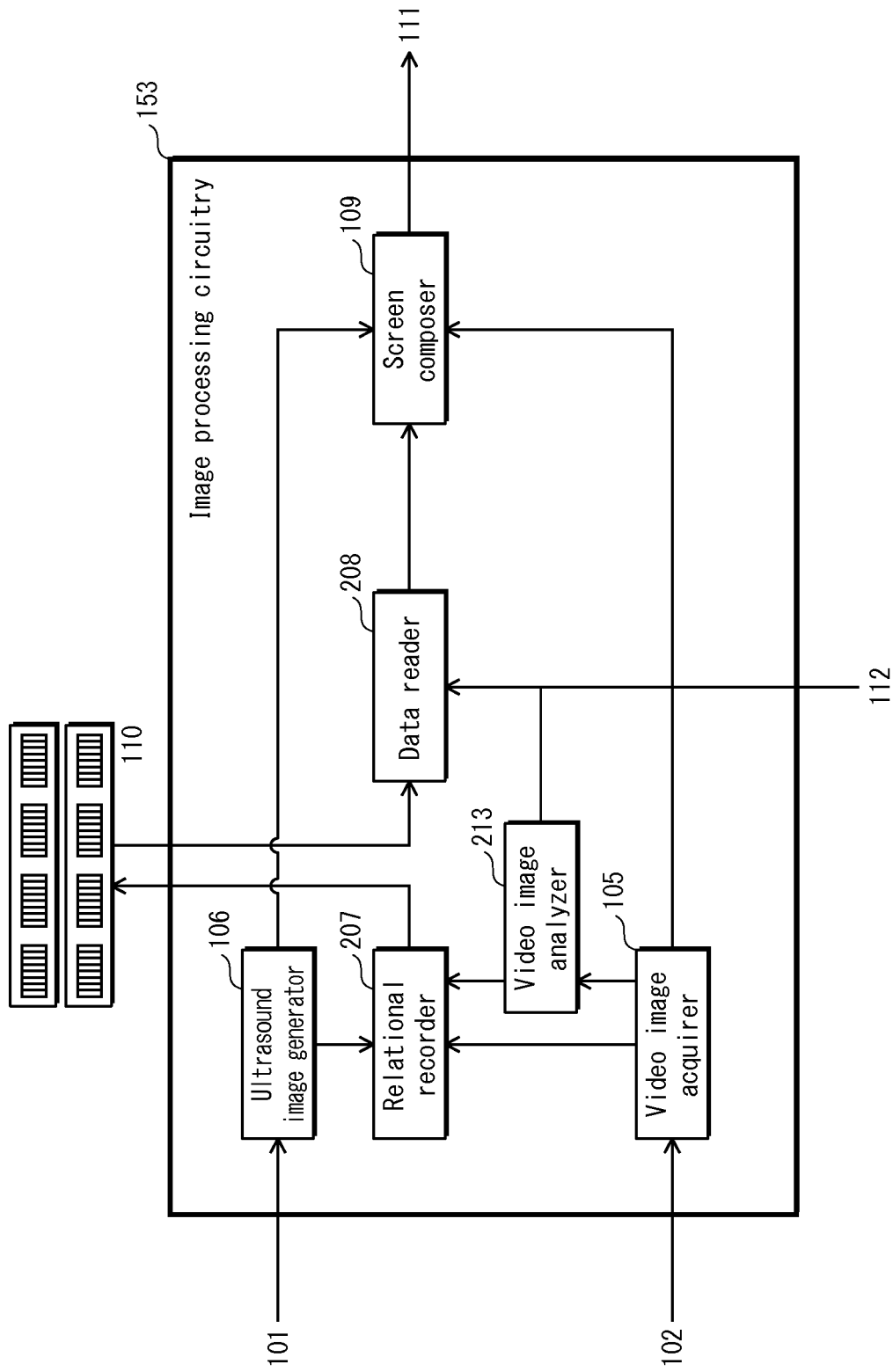
FIG. 10 is a block diagram illustrating configuration of image processing circuitry 153 of the ultrasound diagnostic apparatus 152.

FIG. 9 is a block diagram illustrating configuration of an ultrasound diagnostic system 100 using the ultrasound diagnostic apparatus 152 pertaining to Embodiment 2. FIG. 10 is a block diagram illustrating configuration of image processing circuitry 153 of the ultrasound diagnostic apparatus 152. The ultrasound diagnostic apparatus 152 includes, in addition to the components of the ultrasound diagnostic apparatus 150, the video image analyzer 213 that identifies the examination target part by analyzing video images. This is a difference from the ultrasound diagnostic apparatus 150. Furthermore, the relational recorder 207 and the data reader 208 of the ultrasound diagnostic apparatus 152 have different functions from the relational recorder 107 and the data reader 108 of the ultrasound diagnostic apparatus 150, respectively. In FIG. 9 and FIG. 10, the same elements as in FIG. 1 and FIG. 2 are labeled using the same reference signs and explanation thereof is omitted.

<Configuration of Elements of Ultrasound Diagnostic Apparatus 152>

1. Video Image Analyzer 213

The video image analyzer 213 receives current video images supplied from the video acquirer 105, and identifies the examination target part of the subject to which the probe 101 is currently being applied. Then, the video image analyzer 213 outputs examination target part identification information to the relational recorder 207 and the data reader 208. The examination target part identification information indicates the examination target part of the subject to which the probe 101 is currently being applied. For example, the examination target part identification information indicates, organs such as the stomach, the liver, a lung or the heart, or other parts such as a finger joint of the left hand, a finger joint of the right hand, the left carotid artery, the right carotid artery, the left elbow, the right elbow, the left shoulder, the right shoulder, the left knee, or the right knee. How to identify the examination target part of the subject by analyzing video images is described below.

2. Relational Recorder 207

The relational recorder 207 associates a sequence of ultrasound images and a sequence of video images with each other, and records the images in the data storage 110. The relational recorder 207 also records the examination target part identification information obtained by the video image analyzer 213. In the same manner as the relational recorder 107, the relational recorder 207 may use the storage data list to record the examination target part identification information in addition to the information of the correlation. Specifically, as shown in FIG. 10, the relational recorder 207, as with the relational recorder 107, receives current ultrasound images supplied from the ultrasound image generator 106, current video images acquired from the video acquirer 105, and the examination target part identification information supplied from the video image analyzer 213, and records the received ultrasound images and video images into the data storage 110. These images will serve as reference images in the feature. Simultaneously, the relational recorder 207 adds an additional information set to the storage data list stored in the data storage 110, thereby updating the storage data list. The additional information set contains the information about the relationship between the ultrasound images and the video images as well as the examination target part identification information. Thus, the storage data list stored in the data storage 110 is repeatedly updated by addition of a new additional information set.

Figure 11:
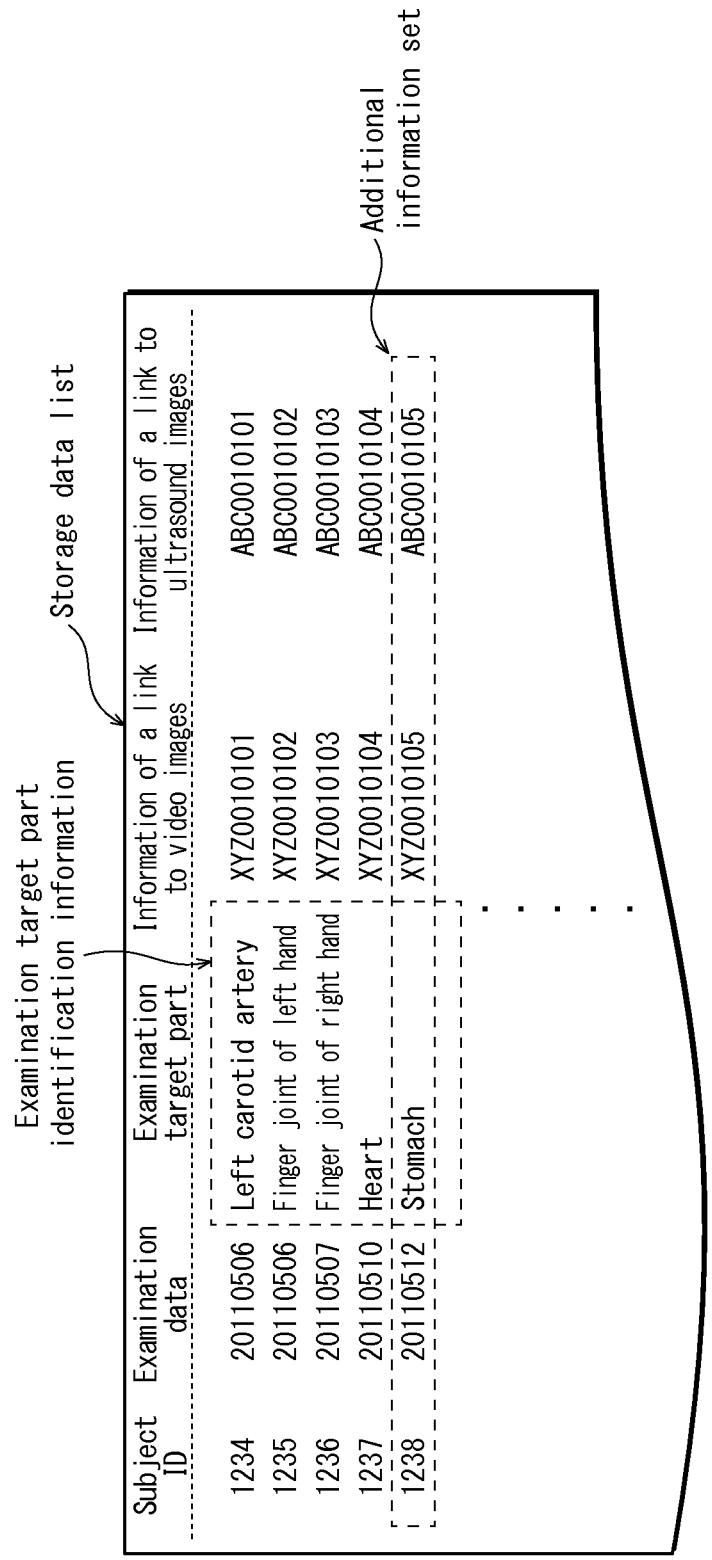
FIG. 11 is a schematic diagram illustrating an example of a storage data list which is output by a relational recorder 207.

FIG. 11 is a schematic diagram illustrating an example of a storage data list which is output by the relational recorder 207. Each information set of the storage data list contains the examination target part identification information in addition to the elements contained in the storage data list recoded by the relational recorder 107, namely the subject ID, the time stamp indicating the examination date, information of a link to video images, and information of a link to ultrasound images. Since the examination target part identification information is recorded together with the information of the link to the ultrasound images and the information of the link to the video images, the ultrasound images and the video images can be searched for by using the examination target part identification information that is associated with them.

Alternatively, the information of the correlation may be recorded by adding, to the ultrasound images, a body mark image that corresponds to the examination target part identification information.

3 Data Reader 208

The data reader 208 receives the examination target part identification information supplied from the video image analyzer 213 and an instruction from the examiner supplied from operation console 112, and reads the reference images stored in the data storage 110. The examiner inputs the subject ID and the examination data to the operation console 112 while seeing the screen displayed on the display device 111, which shows, for example, electronic medical records. The data reader 208 narrows down the list of selectable ultrasound images based on the subject ID and the examination date. Then, the data reader 208 searches for, from among sets of the examination target part identification information recorded in the storage data list, the examination target part identification information that matches the examination target part identification information supplied from the video image analyzer 213 (i.e. the examination target part identification information obtained by analyzing the current video images). Then the data reader 208 reads the reference images corresponding to the examination target part identification information from the data storage 110.

<Operations>

Figure 12:
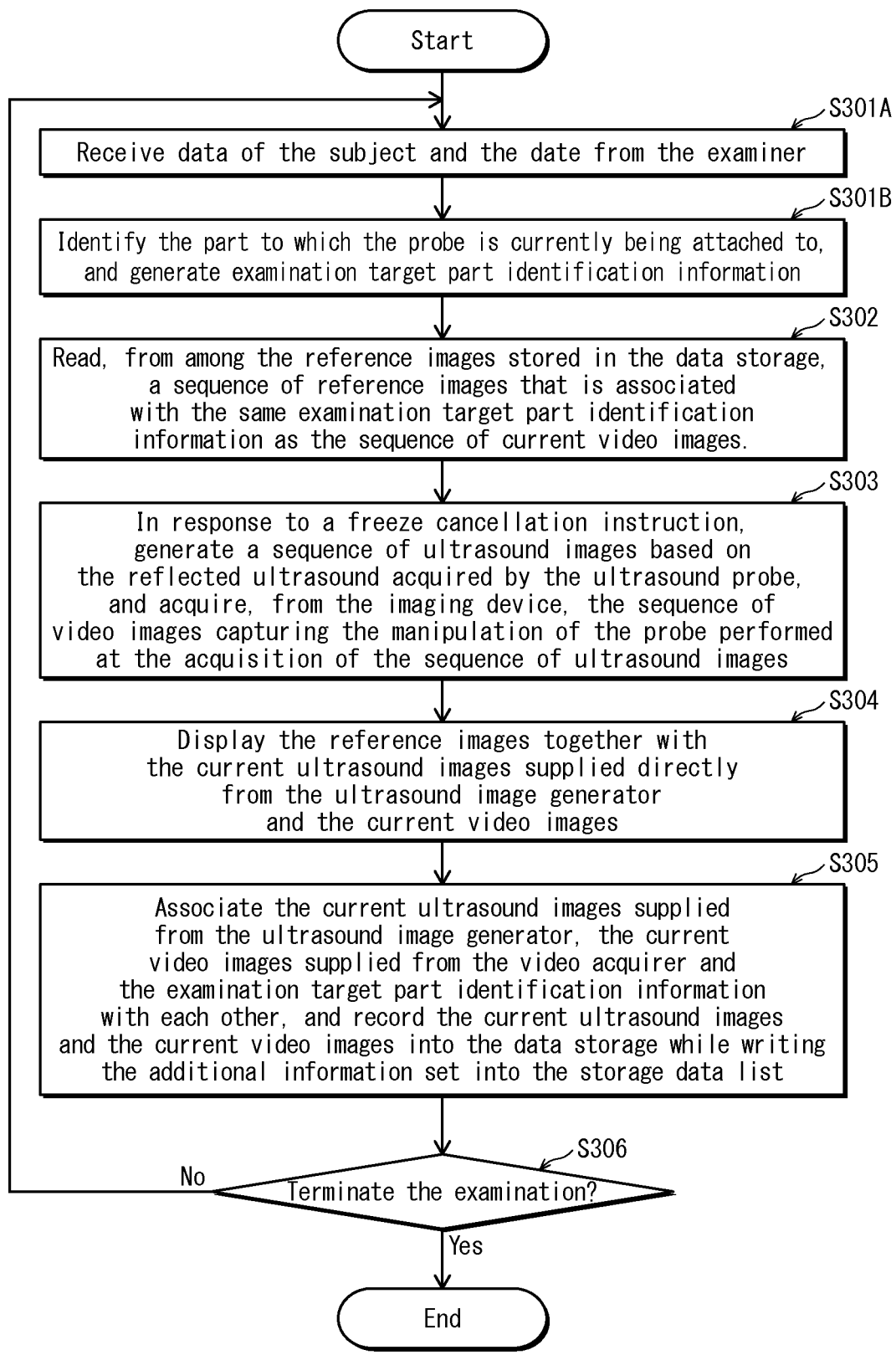
FIG. 12 is a flowchart illustrating processing performed by the ultrasound diagnostic apparatus 152.

Operations of the ultrasound diagnostic apparatus 152 pertaining to Embodiment 2 are described below. FIG. 12 is a flowchart illustrating processing performed by the ultrasound diagnostic apparatus 152.

1. Step S301A

At Step S301A, the examiner inputs data of the subject and the date from the operation console 112. At this stage, the examiner does not manually select desired reference images, and instead specifies the identification information of the subject and the period during which the reference images were acquired. For example, the examiner inputs the subject' name (e.g. Taro Suzuki) and information of the period (e.g. two months ago). Note that the identification information of the subject may be, for example, an ID number. Also, the period may be specified in terms of the order of the examinations, for example by "the most recent examination"

2. Step S301B

At Step S301B, the video image analyzer 213 receives current video images supplied from the video acquirer 105. The current video images capture the manipulation of the probe 101 that is currently being performed. Then, the video image analyzer 213 analyzes the current video images to identify the examination target part to which the probe 101 is currently being attached, thereby creating examination target part identification information.

Figure 13:
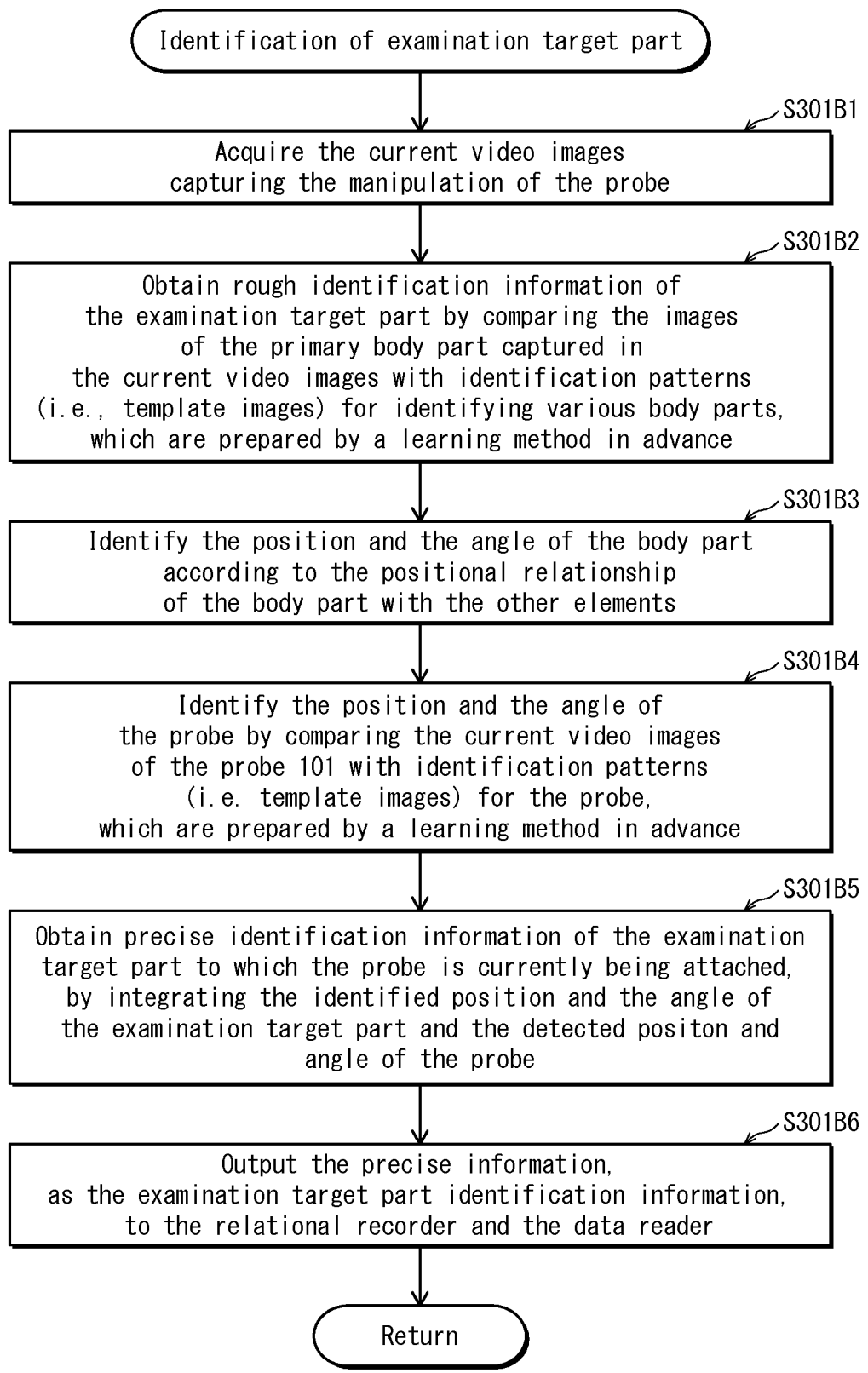
FIG. 13 is a flowchart illustrating details of examination target part identifying processing performed by the ultrasound diagnostic apparatus 152.

FIG. 13 is a flowchart illustrating the details of the examination target part identifying process performed at this step. First, the imaging device 102 starts capturing video images. The examiner moves the probe 101 to the part of the subject's body that the examiner wishes to examine.

At this step, the video image analyzer 213 acquires from the imaging device 102 the current video images capturing the manipulation of the probe 101 (Step S301B1), and obtains rough identification information of the examination target part by comparing the images of the primary body part captured in the current video images with identification patterns (i.e. template images) for identifying various body parts, which are prepared by a learning method in advance (Step S301B2). The rough identification information indicates the primary body part captured in the current video images, such as a finger of the left hand, a finger of the right hand, the left part of the neck, the right part of the neck, the left hand, the right hand, the stomach, the chest, the left leg, the right leg, etc.

Next, the video image analyzer 213 identifies the position and the angle of the body part according to the positional relationship of the body part with the other elements (Step S301B3). Specifically, the video image analyzer 213 identifies the position and the angle of the body part by detecting, for example, the angle (i.e. orientation) of the body part within the video image frames, and the positional relationship of the body part with respect to other elements within the video image frames.

Next, the video image analyzer 213 identifies the position and the angle of the probe 101 by comparing the current video images of the probe 101 with identification patterns (i.e. template images) for the probe 101, which are prepared by a learning method in advance (S301B4).

Next, the video image analyzer 213 obtains precise identification information of the examination target part to which the probe 101 is currently being attached, by integrating the identified position and angle of the examination target part and the detected position and angle of the probe 101 (Step S301B5). The precise identification information of the examination target part indicates the body part to which the probe 101 is currently being attached in further detail, for example organs such as the stomach, the liver, a lung or the heart, or other parts such as a finger joint of the left hand, a finger joint of the right hand, the left carotid artery, the right carotid artery, the left elbow, the right elbow, the left knee, or the right knee.

Finally, the video image analyzer 213 outputs this precise information, as the examination target part identification information, to the relational recorder 207 and the data reader 208 (Step S301B6).

Note that a plurality of imaging devices 102 may be provided for analysis taking the depth of images into consideration. Alternatively, a three-dimensional imaging device may be provided to acquire three-dimensional depth information. The use of depth information in analysis realizes more precise identification.

Note that an additional step may be provided after the Step S301B in order to allow the examiner to check the identification result and correct misidentification. Furthermore, another additional step may be provided of presenting a plurality of candidates and allowing the user to select one from among the candidates.

3. Step S302

At Step S302, the data reader 208 receives the examination target part identification information supplied from the video image analyzer 213, and reads, from among the reference images stored in the data storage 110, a sequence of reference images that is associated with the same examination target part identification information as the sequence of current video images that are currently being acquired. The data storage 110 stores the ultrasound images, the video images and the sets of examination target part identification information, which have been associated with each other in advance. The data reader 208 searches for, from among the sets of examination target part identification information recorded in the storage data list stored in the data storage 110, the examination target part identification information that matches the examination target part identification information supplied from the video image analyzer 213 (i.e. the examination target part identification information obtained by analyzing the current video images). Then the data reader 208 reads, as reference images, the ultrasound images corresponding to the examination target part identification information, and the video images that capture the manipulation of the probe 101 performed during the acquisition of the ultrasound images, from the data storage 110.

Note that the operations illustrated in FIG. 12 are performed repeatedly, and the above-described process of recording the correlation between the ultrasound images and the video images corresponds to Step S305 described below. Thus, at this step, the ultrasound images and video images recorded in the past are treated as reference images.

4. Steps S303 and S304

Steps S303 and S304 are the steps of performing the same operations as Steps S203 and S204 shown in FIG. 5.

The examiner performs an ultrasound examination by comparing the reference images and the current images. At this stage, the video image analyzer 213 has identified the examination target part that the examiner attempts to examine. Therefore, reference images corresponding to the examination target part are displayed on the display device 111. For example, when the examiner attaches the probe 101 to the right knee of the subject, reference images of the right knee are immediately displayed, and when the examiner attaches the probe 101 to the left knee of the subject, reference images of the left knee are immediately displayed. Thus, the examiner can easily refer to the correct reference images corresponding to the current examination target part.

Note that the screen composer 109 may compose a screen according to the examination target part. For example, the screen composer 109 may display a body mark image corresponding to the examination target part identification information on or besides the ultrasound images or video images.

FIG. 14 is a block diagram showing an example screen displayed by the ultrasound diagnostic apparatus 152 pertaining to Embodiment 2. FIG. 14 shows an example screen in which a body mark image corresponding to the reference images of the carotid artery is displayed within a window 205, and similarly a body mark image corresponding to the current ultrasound images of the carotid artery is displayed within a window 206. These body marks displayed on the display device 111 allow the examiner to immediately and correctly recognize the examination target part identified by the video image analyzer 213.

Note that the identification of the examination target part may be continuously performed by the video image analyzer 213 during the period from Step S303 to Step S304.

5. Step S305

At Step S305, the relational recorder 207 associates the ultrasound images and the video images, and stores these images into the data storage 110 after adding the examination target part identification information obtained by the video image analyzer 213. Specifically, the relational recorder 207 associates current ultrasound images supplied from the ultrasound image generator 106 and current video images supplied from the video acquirer 105 with each other, and records the current ultrasound images and the current video images into the data storage 110. Simultaneously, the relational recorder 207 creates an additional information set indicating the correlation between the ultrasound images and the video images as shown in FIG. 11 and the examination target part identification information obtained by the video image analyzer 213, and updates the storage data list stored in the data storage 110 by writing the additional information set into the storage data list.

Note that the relational recorder 207 may associate the ultrasound images and the video images with each other on a frame-to-frame basis. If this is the case, an additional information set is generated for each pair of an ultrasound image as a frame and a video image as a frame, and is recorded into the storage data list stored in the data storage 110.

6. Step S306

At Step S306, the ultrasound examination for the examination target part according to a freeze instruction input by the examiner from the operation console 112. The transceiver 104 stops transmission and reception of ultrasound, and the video acquirer 105 stops image capturing by the imaging device 102. Simultaneously, the relational recorder 207 stops recording the correlation between the current ultrasound images and video images, and stops recording the examination target part identification information.

The ultrasound examination is terminated when the examiner inputs an instruction to terminate the examination from the operation console 112 (Yes at Step S306), and otherwise (No at Step S306) the process is repeated from Step S301A so that examination for another part can be performed.

<Effects>

As described above, the image processing circuitry 153 of the ultrasound diagnostic apparatus 152 includes: an ultrasound image generator 106 that generates a sequence of first ultrasound images from the reflected ultrasound; a video image acquirer 105 that acquires, from the imaging device 102, a sequence of first video images that captures manipulation of the probe 101 performed during generation of the sequence of first ultrasound images; a relational recorder 107 that records, onto the recording medium 110, the sequence of first ultrasound images supplied from the ultrasound image generator 106 and the sequence of first video images supplied from the video image acquirer 105, in association with each other; a data reader 108 that reads a sequence of second ultrasound images and a sequence of second video images from the recording medium 110, the sequence of second ultrasound images being images generated by the ultrasound image generator 106 and recorded onto the recording medium 110 in the past, and the sequence of second video images being video images that capture manipulation of the probe 101 performed during generation of the sequence of second ultrasound images; a screen composer 109 that composes a screen by arranging the sequence of first ultrasound images, the sequence of second ultrasound images, and the sequence of second video images, and displays the screen on the display device 111; and a video analyzer 213 that analyzes the sequence of first video images supplied from the video image acquirer 105 to identify an examination target part of the subject's body, and generates first examination target part identification information indicating the examination target part so identified. The relational recorder 207 additionally records, onto the recording medium 110, the first examination target part identification information in association with the sequence of first ultrasound images and the sequence of first video images, and the data reader 208 reads, from the recording medium 110, a pair of a sequence of second ultrasound images and a sequence of second video images that is associated with second examination target part identification information that matches the first examination target part identification information, the sequence of second ultrasound images being images generated by the ultrasound image generator 106 and recorded onto the recording medium 110 in the past, and the sequence of second video images being video images that capture manipulation of the probe 101 performed during generation of the sequence of second ultrasound images.

That is, the video image analyzer 213 identifies the examination target part by analyzing the sequence of video images that is currently being acquired, and stores the sequence of ultrasound images into the data storage 110 in association with the examination target part. Furthermore, any of sequences of reference images acquired in the past can be referred to according to the examination target part.

Due to the stated configuration, the examination target part that the examiner attempts to examine is identified, and therefore, the examiner can easily view the correct reference images corresponding to the examination target part. As a result, the examiner can perform an accurate comparison examination.

The recording medium 110 may store thereon body mark images. The data reader 208 may read, from among the body mark images stored on the recording medium 110, a body mark image corresponding to the second examination target part identification information. The screen composer 109 may compose the screen by additionally arranging the body mark image corresponding to the second examination target part identification information.

The stated configuration allows the examiner to immediately and correctly recognize the examination target part identified by the video image analyzer 213, by referring to the body marks displayed on the display device 111.

Other Modified Examples

In the ultrasound diagnostic apparatus pertaining to the above embodiment, the data storage 110 which is an example of a storage device is included in the ultrasound diagnostic apparatus. However, the storage device is not limited to such a configuration and may alternatively be a semiconductor memory, a hard disk drive, an optical disk drive, a magnetic storage device, or the like that is connected to the ultrasound diagnostic apparatus from externally thereto.

Furthermore, although an example of configuration is explained in which the ultrasound probe 101 and the display device 111 are connected to the ultrasound diagnostic apparatus from externally thereto, alternatively the aforementioned elements may all be integrated into the ultrasound diagnostic apparatus.

The probe 101 may also include an inclination angle measurer such as an angle sensor and an inclination angle of the probe 101 which is measured may be recorded in examination results.

In the embodiment described above, the probe 101 includes a plurality of piezoelectric elements that are arranged in a one-dimensional array. However, the probe 101 is not limited to such a configuration. For example, the probe 101 may include a two-dimensional transducer in which a plurality of piezoelectric elements are arranged in a two-dimensional array, or an oscillating ultrasound probe that has a plurality of transducers arranged in a one-dimensional array and acquires three-dimensional ultrasound images while mechanically oscillating the transducers. The configuration of the probe 101 may be selected according to the measurement to be performed. For example, in a configuration in which the probe includes piezoelectric elements arranged in a two-dimensional array, irradiation position and direction of a transmitted ultrasound beam can be controlled by adjusting magnitude and timing of voltage application to each of the piezoelectric elements.

Also, the probe may have some of the functions of the transceiver. For example, the probe may generate a transmission electrical signal based on a control signal output from the transceiver for generation of the transmission electrical signal, and may convert the transmission electrical signal to ultrasound. The probe may also convert reflected ultrasound received thereby to a reception electrical signal, and may generate a reception signal based on the reception electrical signal.

Typically the components included in the ultrasound diagnostic apparatus pertaining to each embodiment are implemented through a large scale integration (LSI) which is a type of integrated circuit (IC). Each of the components may be integrated individually into a single chip. Alternatively, some or all of the components may be collectively integrated into a single chip.

The embodiments were explained for examples in which each block is an independent piece of hardware. However, the blocks included in the ultrasound diagnostic apparatus are not limited to being independent pieces of hardware. For example, functions of each of the blocks may be implemented as necessary through a combination of a CPU and software.

With regards to functional blocks included in the ultrasound diagnostic apparatus, typically a portion or all of the functions of the functional blocks can be implemented through an LSI. Each of the functional blocks may be integrated individually into a single chip. Alternatively, some or all of the functional blocks may be collectively integrated into a single chip. Note that depending on the degree of integration, an LSI may be referred to as an IC, a system LSI, a super LSI, or an ultra LSI.

Furthermore, the method of circuit integration is not limited to an LSI and may alternatively be implemented through a dedicated circuit or a general processor. A field programmable gate array (FPGA) which is programmable after the LSI is manufactured or a reconfigurable processor which allows for reconfiguration of the connection and setting of circuit cells inside the LSI may alternatively be used.

Furthermore, if technology for forming integrated circuits that replaces LSI were to emerge, owing to advances in semiconductor technology or to another derivative technology, the integration of functional blocks may naturally be accomplished using such technology.

Also, a portion or all of the functions of the ultrasound diagnostic apparatus pertaining to each embodiment may be implemented through execution of a program by a processor such as a CPU.

Furthermore, the present invention may alternatively be implemented as the aforementioned program or as a non-transitory computer recordable recording medium on which the program is recorded. Of course, the aforementioned program can also be distributed through a transfer medium such as the Internet.

Note that block diagrams referred to herein only illustrate one example of division of functional blocks. A plurality of the functional blocks may alternatively be implemented in combination as a single functional block, and likewise each one of the functional blocks may alternatively be divided and implemented as a plurality of separate functional blocks. Also, a portion of the functions of one of the functional blocks may be transferred to any other of the functional blocks. A single piece of hardware or software may be used to process functions of a plurality of functional blocks that have similar functions either in parallel or through a time division method.

Note that the order of steps described above is provided merely for explanation of one specific example of the present invention and such steps may alternatively be performed in a different order. Also, part of one of the aforementioned steps may be performed at the same time as (in parallel to) a different one of the aforementioned steps.

Functions of the ultrasound diagnostic apparatus pertaining to the embodiments and the modified examples thereof may be at least partially combined. Furthermore, the numerical values given above are intended only for describing a specific example of the disclosure, and do not represent any limitation to the given values.

Of course the present invention also includes various modified examples of the embodiments which are within the scope of modifications that a person having ordinary skill in the art might consider.

Conclusion

As described above, an ultrasound diagnostic apparatus pertaining to one aspect of the present disclosure is an ultrasound diagnostic apparatus that is connectable to a probe 101, an imaging device 102, a recording medium 110, and a display device 111, and that obtains and displays ultrasound images of inside a subject's body by transmitting ultrasound towards the subject's body via the probe 101 and receiving reflected ultrasound, the ultrasound diagnostic apparatus comprising image processing circuitry that includes: an ultrasound image generator 106 that generates a sequence of first ultrasound images from the reflected ultrasound; a video image acquirer 105 that acquires, from the imaging device 102, a sequence of first video images that captures manipulation of the probe 101 performed during generation of the sequence of first ultrasound images; a relational recorder 107 that records, onto the recording medium 110, the sequence of first ultrasound images supplied from the ultrasound image generator 106 and the sequence of first video images supplied from the video image acquirer 105, in association with each other; a data reader 108 that reads a sequence of second ultrasound images and a sequence of second video images from the recording medium 110, the sequence of second ultrasound images being images generated by the ultrasound image generator 106 and recorded onto the recording medium 110 in the past, and the sequence of second video images being video images that capture manipulation of the probe 101 performed during generation of the sequence of second ultrasound images; and a screen composer 109 that composes a screen by arranging the sequence of first ultrasound images, the sequence of second ultrasound images, and the sequence of second video images, and displays the screen on the display device 111. The screen composer 109 may compose the screen by additionally arranging the sequence of first video images.

This configuration allows the examiner to correctly know the movement of the examination target part of the subject and the manipulation of the probe that were performed during the acquisition of ultrasound images for comparison examination in an ultrasound examination. Therefore, the ultrasound diagnostic apparatus enables the examiner to reproduce the manipulation of the probe and the movement of the examination target part performed during an examination in the past, thereby realizing an ultrasound examination at a high level of accuracy and reproducibility.

This configuration also allows the examiner to perform an ultrasound examination while comparing, on the same screen, a sequence of video images that captures the manipulation of the probe performed during an examination recorded in the past and the sequence of video images that captures the manipulation of the probe that is currently acquiring the sequence of ultrasound images. This makes it further easier for the examiner to reproduce the manipulation of the probe performed during an examination in the past. Therefore, the examiner can swiftly and easily perform an accurate comparison examination.

<Supplement>

The embodiments described above are merely preferable examples of the present invention. Values, forms, materials, components, component positions and connections, steps, step order, etc., illustrated in the embodiments represent examples and do not limit the spirit of the present invention. Further, among components of each embodiment, processes not disclosed in independent claims reciting top-level concepts of the present invention are described as components for further beneficial effect.

Further, to aid in understanding the invention, reduced scale components of each image of the embodiment may differ from actual implementation. Further, disclosure of the above embodiments is not a limitation and may be appropriately changed within the scope of the spirit of the present invention.

Furthermore, although materials such as circuit parts on a substrate, lead wires, etc., do exist in the ultrasound diagnostic apparatus, electrical wiring and electric circuits may have a wide variety of implementations based on common knowledge in the technical field, and are therefore omitted from the description as they have no direct relevance to description of the present invention. Note that each drawing described above is schematic, and is not an exact representation.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound diagnostic apparatus that is connectable to a probe, an imaging device, a recording medium, and a display device, and that obtains and displays ultrasound images of inside a subject's body by transmitting ultrasound towards the subject's body via the probe and receiving reflected ultrasound, the ultrasound diagnostic apparatus comprising image processing circuitry that includes:
an ultrasound image generator that generates a sequence of first ultrasound images from the reflected ultrasound;
a video image acquirer that acquires, from the imaging device, a sequence of first video images that captures manipulation of the probe performed during generation of the sequence of first ultrasound images;
a relational recorder that records, onto the recording medium, the sequence of first ultrasound images supplied from the ultrasound image generator and the sequence of first video images supplied from the video image acquirer, in association with each other;
a data reader that reads a sequence of second ultrasound images and a sequence of second video images from the recording medium, the sequence of second ultrasound images being images generated by the ultrasound image generator and recorded onto the recording medium in the past, and the sequence of second video images being video images that capture manipulation of the probe performed during generation of the sequence of second ultrasound images; and
a screen composer that composes a screen by arranging the sequence of first ultrasound images, the sequence of second ultrasound images, and the sequence of second video images, and displays the screen on the display device.

2. The ultrasound diagnostic apparatus of claim 1, wherein
the screen composer composes the screen by additionally arranging the sequence of first video images.

3. The ultrasound diagnostic apparatus of claim 1, wherein
the image processing circuitry further includes a video analyzer that analyzes the sequence of first video images supplied from the video image acquirer to identify an examination target part of the subject's body, and generates first examination target part identification information indicating the examination target part so identified,
the relational recorder additionally records, onto the recording medium, the first examination target part identification information in association with the sequence of first ultrasound images and the sequence of first video images, and
the data reader reads, from the recording medium, a pair of a sequence of second ultrasound images and a sequence of second video images that is associated with second examination target part identification information that matches the first examination target part identification information, the sequence of second ultrasound images being images generated by the ultrasound image generator and recorded onto the recording medium in the past, and the sequence of second video images being video images that capture manipulation of the probe performed during generation of the sequence of second ultrasound images.

4. The ultrasound diagnostic apparatus of claim 3, wherein
the recording medium stores thereon body mark images,
the data reader reads, from among the body mark images stored on the recording medium, a body mark image corresponding to the second examination target part identification information, and the screen composer composes the screen by additionally arranging the body mark image corresponding to the second examination target part identification information.

5. An ultrasound image processing method used in an ultrasound diagnostic apparatus that is connectable to a probe, an imaging device, a recording medium, and a display device, and that obtains and displays ultrasound images of inside a subject's body by transmitting ultrasound towards the subject's body via the probe and receiving reflected ultrasound, comprising:

generating a sequence of first ultrasound images from the reflected ultrasound;

acquiring, from the imaging device, a sequence of first video images that captures manipulation of the probe performed during generation of the sequence of first ultrasound images;

recording, onto the recording medium, the sequence of first ultrasound images and the sequence of first video images, in association with each other;

reading a sequence of second ultrasound images and a sequence of second video images from the recording medium, the sequence of second ultrasound images being images generated and recorded onto the recording medium in the past, and the sequence of second video images being video images that capture manipulation of the probe performed during generation of the sequence of second ultrasound images; and composing a screen by arranging the sequence of first ultrasound images, the sequence of second ultrasound images, and the sequence of second video images, and displaying the screen on the display device.

6. A non-transitory computer readable recording medium on which is recorded a program for causing a computer to perform the ultrasound image processing method of claim 5.

* * * * *